(12) United States Patent
Shiraki

(10) Patent No.: US 12,150,617 B2
(45) Date of Patent: Nov. 26, 2024

(54) MEDICAL INFORMATION PROCESSING APPARATUS, MEDICAL INFORMATION PROCESSING METHOD, AND MEDICAL INFORMATION PROCESSING PROGRAM

(71) Applicant: Sony Group Corporation, Tokyo (JP)

(72) Inventor: Hisakazu Shiraki, Tokyo (JP)

(73) Assignee: Sony Group Corporation, Tokyo (JP)

( * ) Notice: Subject to any disclaimer, the term of this patent is extended or adjusted under 35 U.S.C. 154(b) by 114 days.

(21) Appl. No.: 17/639,585

(22) PCT Filed: Oct. 6, 2020

(86) PCT No.: PCT/JP2020/037804
§ 371 (c)(1),
(2) Date: Mar. 2, 2022

(87) PCT Pub. No.: WO2021/075306
PCT Pub. Date: Apr. 22, 2021

(65) Prior Publication Data
US 2022/0296082 A1    Sep. 22, 2022

(30) Foreign Application Priority Data

Oct. 17, 2019   (JP) .................................. 2019-189952

(51) Int. Cl.
*A61B 1/00*          (2006.01)
*A61B 90/20*         (2016.01)

(52) U.S. Cl.
CPC .... *A61B 1/000095* (2022.02); *A61B 1/00006* (2013.01); *A61B 1/00045* (2013.01); *A61B 1/00163* (2013.01); *A61B 90/20* (2016.02)

(58) Field of Classification Search
CPC .......... A61B 1/000095; A61B 1/00006; A61B 1/00045; A61B 1/00163; A61B 90/20
See application file for complete search history.

(56) References Cited

U.S. PATENT DOCUMENTS 5,172,418 A     12/1992 Ito
10,750,930 B2 *  8/2020 Takahashi ............ A61B 1/0051
(Continued)

FOREIGN PATENT DOCUMENTS

EP         3437546 A1    2/2019
JP      2000-287202 A   10/2000
(Continued)

OTHER PUBLICATIONS

International Search Report and Written Opinion mailed on Dec. 22, 2020, received for PCT Application PCT/JP2020/037804, Filed on Oct. 6, 2020, 11 pages including English Translation.

*Primary Examiner* — Brian P Yenke
(74) *Attorney, Agent, or Firm* — XSENSUS LLP

(57) ABSTRACT

A surgical information processing apparatus according to the present disclosure includes: an acquisition unit that acquires a surgical image; a determination unit that determines whether additional information is attached to the surgical image acquired by the acquisition unit; and a processing unit that performs first image processing when the determination unit has determined that the additional information is not attached, and does not perform the first image processing when the determination unit has determined that the additional information is attached.

20 Claims, 17 Drawing Sheets

(56) References Cited

U.S. PATENT DOCUMENTS

| | | | |
|---|---|---|---|
| 10,904,437 B2* | 1/2021 | Ikeda | H04N 23/6811 |
| 11,123,150 B2* | 9/2021 | Ichiki | H04N 23/74 |
| 11,301,964 B2* | 4/2022 | Ikeda | G06T 5/003 |
| 2004/0125877 A1* | 7/2004 | Chang | G06F 16/739 |
| | | | 348/E5.065 |
| 2005/0281477 A1* | 12/2005 | Shiraki | G06T 5/003 |
| | | | 382/255 |
| 2014/0108053 A1 | 4/2014 | Akaki | |
| 2015/0264264 A1* | 9/2015 | Shiraki | G06V 10/141 |
| | | | 348/68 |
| 2018/0049629 A1* | 2/2018 | Nakagawa | A61B 1/000094 |
| 2018/0220872 A1* | 8/2018 | Tashiro | A61B 1/00045 |
| 2019/0099060 A1* | 4/2019 | Yaguchi | G06T 7/0012 |
| 2019/0164002 A1* | 5/2019 | Choi | G06F 40/58 |
| 2020/0069160 A1* | 3/2020 | Oosake | A61B 1/000094 |
| 2020/0163538 A1* | 5/2020 | Takahashi | A61B 1/043 |
| 2021/0106208 A1* | 4/2021 | Iwaki | A61B 1/00045 |
| 2021/0145248 A1* | 5/2021 | Ito | A61B 1/000094 |
| 2021/0153720 A1* | 5/2021 | Usuda | A61B 1/07 |
| 2021/0153722 A1* | 5/2021 | Karino | G06T 19/20 |
| 2021/0235980 A1* | 8/2021 | Oosake | A61B 1/05 |
| 2021/0295980 A1* | 9/2021 | Ichikawa | G16H 40/63 |
| 2021/0297606 A1* | 9/2021 | Yamada | A61B 90/20 |
| 2021/0307863 A1* | 10/2021 | Ben-Yishai | G06V 10/443 |
| 2022/0392617 A1* | 12/2022 | Asai | G16H 40/20 |
| 2023/0121709 A1* | 4/2023 | Xu | H04N 21/2187 |
| | | | 600/103 |

FOREIGN PATENT DOCUMENTS

| | | |
|---|---|---|
| JP | 2003-58866 A | 2/2003 |
| JP | 2005-11309 A | 1/2005 |
| JP | 2007-185215 A | 7/2007 |
| JP | 2007-296079 A | 11/2007 |
| JP | 2007-313133 A | 12/2007 |
| JP | 2008-188329 A | 8/2008 |
| JP | 2011-156262 A | 8/2011 |
| JP | 2013-90035 A | 5/2013 |
| JP | 2013-165755 A | 8/2013 |
| JP | 2016-218702 A | 12/2016 |
| JP | 2017-108792 A | 6/2017 |
| JP | 2017-185254 A | 10/2017 |
| WO | 2017/169139 A1 | 10/2017 |
| WO | 2018/043205 A1 | 3/2018 |
| WO | 2018/211885 A1 | 11/2018 |
| WO | WO-2018211709 A1 | 11/2018 |

* cited by examiner

| THRESHOLD ID | TARGET | THRESHOLD | ... |
|---|---|---|---|
| TH1 | ABSOLUTE DIFFERENCE (FIRST THRESHOLD) | VL1 | ... |
| TH2 | LUMINANCE (SECOND THRESHOLD) | VL2 | ... |
| ... | ... | ... | ... |

MEDICAL INFORMATION PROCESSING APPARATUS, MEDICAL INFORMATION PROCESSING METHOD, AND MEDICAL INFORMATION PROCESSING PROGRAM

CROSS-REFERENCE TO RELATED APPLICATIONS

The present application is based on PCT filing PCT/JP2020/037804, filed Oct. 6, 2020, which claims priority to Japanese Application No. 2019-189952, filed Oct. 17, 2019, the entire contents of each are incorporated herein by reference.

FIELD

The present disclosure relates to a surgical information processing apparatus, a surgical information processing method, and a surgical information processing program.

BACKGROUND

Regarding medical observation devices such as endoscopes and microscopes, various types of image processing have been proposed for improving the efficiency of surgery. For example, vibrations such as camera shake or floor vibration cause disturbance (image blur) in a captured image. In particular, along with a trend of higher definition in medical observation device images in recent years, there has been an increased influence of image blurs on the visibility of images. To handle this, image blur correction processing has been proposed. In addition, some surgical methods require rotation of a display image of the medical observation device. Therefore, image rotation correction processing has been proposed. In this manner, there have been proposed various techniques of performing image processing such as correction processing in order to improve the efficiency of surgery.

CITATION LIST

Patent Literature

Patent Literature 1: JP 2017-185254 A

SUMMARY

Technical Problem

According to the known technology, there has been proposed an endoscope in which a gyro is provided in a camera head of a medical observation device or the like, and camera shake is detected by the gyro to perform camera shake correction on an output image (for example, Patent Literature 1).

However, the known technology is not considered to be able to always perform image processing appropriately according to a surgical image. The known technology performs camera shake on a surgical image in which camera shake is detected, and thus, when stationary information such as character information is attached to the surgical image, there is a problem of occurrence of blur in the stationary information due to camera shake correction. In this manner, simply applying image processing such as camera shake correction on a surgical image may not always be appropriate image processing.

In view of these, the present disclosure proposes a surgical information processing apparatus, a surgical information processing method, and a surgical information processing program capable of appropriately performing image processing according to a surgical image.

Solution to Problem

According to the present disclosure, a surgical information processing apparatus includes an acquisition unit that acquires a surgical image; a determination unit that determines whether additional information is attached to the surgical image acquired by the acquisition unit; and a processing unit that performs first image processing when the determination unit has determined that the additional information is not attached, and does not perform the first image processing when the determination unit has determined that the additional information is attached.

DESCRIPTION OF EMBODIMENTS

Embodiments of the present disclosure will be described below in detail with reference to the drawings. Note that the surgical information processing apparatus, the surgical information processing method, and the surgical information processing program according to the present application are not limited by this embodiment. Moreover, in each of the following embodiments, the same parts are denoted by the same reference symbols, and a repetitive description thereof will be omitted.

The present disclosure will be described in the following order.

1. First Embodiment
1-1. Overview of information processing according to first embodiment of present disclosure
1-1-1. Target and effects of information processing
1-1-2. Other determination examples
1-2. Configuration of surgical information processing system according to first embodiment
1-3. Configuration of surgical information processing apparatus according to first embodiment
1-4. Procedure of information processing according to first embodiment
1-5. Example of specific configuration of surgical information processing system
1-6. Conceptual diagram of functional configuration example of the surgical information processing system
1-6-1. Assumable field for implementation of surgical information processing system
1-6-2. Surgical information processing apparatus
1-6-3. Determination of surgical image
1-6-4. Detection of superimposition region
1-6-5. User notification unit and user IF
1-6-6. Processing determination unit
1-6-7. Image processing execution unit
1-7. Processing mode examples of image processing
1-7-1. First processing mode
1-7-2. Second processing mode
1-7-3. Third processing mode
1-7-4. Fourth processing mode
2. Second Embodiment
2-1. Configuration of surgical information processing apparatus according to second embodiment of present disclosure
2-2. Conceptual diagram of functional configuration example of surgical information processing system
3. Other embodiments
3-1. Determination example based on luminance
3-1-1. Conceptual diagram of functional configuration example of surgical information processing system
3-1-2. Example of determination based on luminance
3-2. Other configuration examples
3-3. Others
4. Effects according to present disclosure
5. Hardware configuration 1. First Embodiment

[1-1. Overview of Information Processing According to First Embodiment of Present Disclosure]

Figure 1:
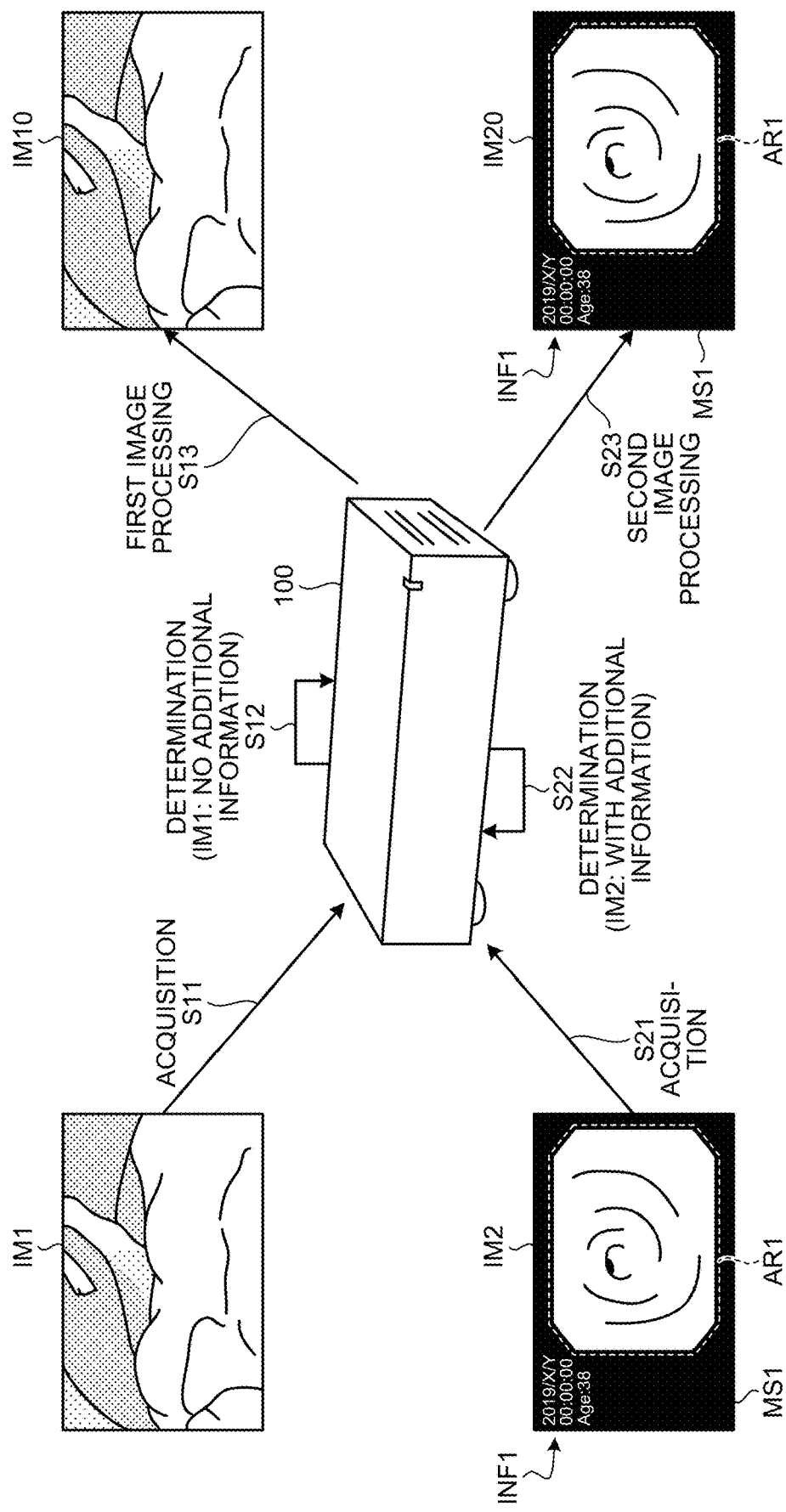
FIG. 1 is a diagram illustrating an example of information processing according to a first embodiment of the present disclosure.

FIG. 1 is a diagram illustrating an example of information processing according to a first embodiment of the present disclosure. Information processing according to the first embodiment of the present disclosure is implemented by a surgical information processing apparatus 100 illustrated in FIG. 1.

The surgical information processing apparatus 100 is a surgical information processing apparatus (also simply referred to as "information processing apparatus") that executes information processing according to the first embodiment. In the example of FIG. 1, in a case where it is determined that additional information is not attached (provided) to a surgical image, the surgical information processing apparatus 100 performs image processing adapted to the cases with no additional information (hereinafter, also referred to as "first image processing"). In addition, in a case where it is determined that additional information is attached, the surgical information processing apparatus 100 does not perform the first image processing, and performs image processing adapted to the cases with additional information (hereinafter, also referred to as "second image processing").

Furthermore, the example of FIG. 1 illustrates a case where the surgical information processing apparatus 100 determines whether additional information is attached to a surgical image such as a moving image obtained by imaging a site to be subjected to a surgical operation, as a target. Although the example of FIG. 1 illustrates a case where character information is provided as an example of additional information, the additional information may be any information as long as the information is attached (provided) to an image captured by a medical observation device 10 (refer to FIG. 2) or the like.

Hereinafter, the processing illustrated in FIG. 1 will be specifically described. An example of FIG. 1 will describe an exemplary case where an acquired image has been determined to be a surgical image. Incidentally, the surgical information processing apparatus 100 may also determine whether the acquired image is a surgical image before the determination of the presence/absence of additional information, and details of which will be described below. First, the surgical information processing apparatus 100 acquires a surgical image IM1 (step S11). For example, the surgical information processing apparatus 100 acquires the surgical image IM1 from the medical observation device 10. The surgical information processing apparatus 100 acquires the surgical image IM1 obtained by imaging, by using an endoscope, a site to be subjected to a surgical operation.

Subsequently, the surgical information processing apparatus 100 determines whether additional information is attached to the surgical image IM1 (step S12). The surgical information processing apparatus 100 determines whether additional information is attached to the surgical image IM1 based on the surgical image IM1. For example, the surgical information processing apparatus 100 determines whether additional information is attached to the surgical image IM1 based on comparison between a plurality of images including the surgical image IM1.

For example, the surgical information processing apparatus 100 determines whether additional information is attached to the surgical image IM1 based on a difference from an image captured earlier than the surgical image IM1. For example, the surgical information processing apparatus 100 calculates a difference of each pixel between images of each frame, and determines whether additional information is attached based on an integrated value of the differences in the pixels. For example, the surgical information processing apparatus 100 calculates an absolute difference of each pixel between an image of each frame and an image of the preceding frame of the frame. Subsequently, the surgical information processing apparatus 100 integrates the absolute difference for each pixel. The number of images (number of frames) to be integrated may be appropriately set by the number of images, the number of seconds, or the like. For example, the number of images (number of frames) to be integrated may be appropriately set to three seconds, 180 frames (sheets), or the like. By comparing the absolute difference integrated for each pixel with a threshold, the surgical information processing apparatus 100 determines whether additional information is attached. In a case where there is a region (corresponding region) in which the absolute difference is less than the threshold, the surgical information processing apparatus 100 determines that the additional information is attached. The surgical information processing apparatus 100 may determine that the additional information is attached in a case where the corresponding region has a predetermined size or more. The surgical information processing apparatus 100 may determine that additional information is not attached in a case where the corresponding region is less than a predetermined size. In this manner, the surgical information processing apparatus 100 acquires a plurality of surgical images including the surgical image IM1 and compares the plurality of surgical images to determine whether additional information is attached to the surgical image IM1. Note that the above is an example, and the surgical information processing apparatus 100 may determine attachment of the additional information by using various types of information as appropriate.

In the example of FIG. 1, the surgical information processing apparatus 100 determines that no additional information is attached to the surgical image IM1. Therefore, the surgical information processing apparatus 100 performs first image processing on the surgical image IM1 (step S13). For example, the surgical information processing apparatus 100 performs first image processing on an entire portion of the surgical image IM1. The surgical information processing apparatus 100 executes camera shake correction as the first image processing on the entire portion of the surgical image IM1. With this processing, the surgical information processing apparatus 100 generates a surgical image IM10 that has undergone the first image processing. Note that specific processing performed as the first image processing is not limited to the camera shake correction, and may be various types of processing. For example, the specific processing performed as the first image processing may be zooming, rotation correction, processing of adding picture in picture (PinP), and the like. In this manner, the specific processing performed as the first image processing is not limited to the camera shake correction, and may be various types of processing such as image magnification processing by digital zoom, rotation correction processing on an image, and processing of adding another image to an image.

Figure 2:
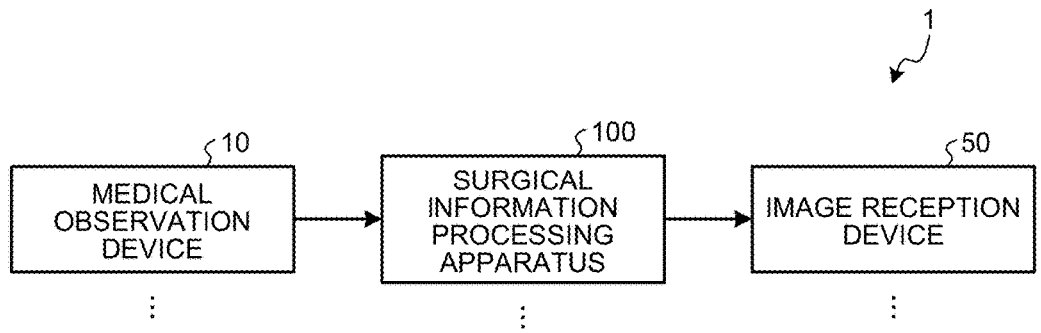
FIG. 2 is a diagram illustrating a configuration example of a surgical information processing system according to the first embodiment.

Next, the surgical information processing apparatus 100 transmits the surgical image IM10 that has undergone the first image processing to an image reception device 50 (refer to FIG. 2). For example, the surgical information processing apparatus 100 transmits the surgical image IM10 that has undergone the first image processing to the image reception device 50 as a display device. The image reception device 50 that has received the surgical image IM10 from the surgical information processing apparatus 100 displays the surgical image IM10.

The surgical information processing apparatus 100 acquires a surgical image IM2 (step S21). For example, the surgical information processing apparatus 100 acquires the surgical image IM2 from the medical observation device 10. The surgical information processing apparatus 100 acquires the surgical image IM2, which is based on an image captured by the medical observation device 10 and in which a mask MS1 being an electronic mask (hereinafter also simply referred to as "mask") is applied and character information INF1 is attached. For example, the mask MS1 is an electronic mask (mask image) attached to an image by mask processing, and is information (image information) for masking a region other than a predetermined region in the image with a specific color (black in FIG. 1). The surgical information processing apparatus 100 acquires the surgical image IM2 which is based on an image captured by the medical observation device 10 and in which the character information INF1 is attached by using a device having an image processing function, such as a camera control unit 200 (refer to FIG. 8). For example, the character information INF1 is on-screen display (OSD) information (hereinafter also simply referred to as "OSD"). Note that the OSD information is not limited to character information, and may be an icon or the like. The OSD information may be various information such as information indicating a predetermined graphic or a predetermined color. In the example of FIG. 1, the surgical information processing apparatus 100 acquires the surgical image IM2 in which portions other than a region AR1 are masked by the mask MS1 and the character information INF1 is attached.

Subsequently, the surgical information processing apparatus 100 determines whether additional information is attached to the surgical image IM2 (step S22). The surgical information processing apparatus 100 determines whether additional information is attached to the surgical image IM2 based on the surgical image IM2. As described above, the surgical information processing apparatus 100 integrates the absolute difference for each pixel. By comparing the absolute difference integrated for each pixel with a threshold, the surgical information processing apparatus 100 determines whether additional information is attached. Furthermore, the surgical information processing apparatus 100 may determine that a region in which the absolute difference is a threshold or more is a surgical region. In the example of FIG. 1, the surgical information processing apparatus 100 may determine the region AR1 as a surgical region.

In the example of FIG. 1, the surgical information processing apparatus 100 determines that additional information is attached to the surgical image IM2. Accordingly, the surgical information processing apparatus 100 performs second image processing on the surgical image IM2 (step S23). For example, the surgical information processing apparatus 100 executes second image processing of performing the same type of image processing as the first image processing on a part of the image. For example, the surgical information processing apparatus 100 executes second image processing of performing the same type of image processing as the first image processing on the region AR1 of the surgical image IM2. For example, the surgical information processing apparatus 100 executes the camera shake correction only on the region AR1 of the surgical image IM2. The surgical information processing apparatus 100 does not perform the camera shake correction on the character information INF1. For example, the surgical information processing apparatus 100 does not execute the camera shake correction on regions other than the region AR1 of the surgical image IM2. With this configuration, the surgical information processing apparatus 100 generates a surgical image IM20 that has undergone the second image processing. Note that the surgical information processing apparatus 100 may execute or does not have to execute image processing on portions other than the region where the character information INF1 of the mask MS1 is arranged.

Subsequently, the surgical information processing apparatus 100 transmits the surgical image IM20 that has undergone the second image processing to the image reception device 50 (refer to FIG. 2). For example, the surgical information processing apparatus 100 transmits the surgical image IM20 that has undergone the second image processing to the image reception device 50 as a display device. The image reception device 50 that has received the surgical image IM20 from the surgical information processing apparatus 100 displays the surgical image IM20.

1-1-1. Target and Effects of Information Processing

As described above, the surgical information processing apparatus 100 performs the first image processing when it is determined that additional information is not attached to the surgical image, and performs the second image processing when it is determined that additional information is attached to the surgical image. With this configuration, the surgical information processing apparatus 100 can appropriately perform image processing according to the surgical image.

For example, there is no problem when the medical observation device includes a function of image processing such as a camera shake correction function. However, in a case where the medical observation device does not have a function of image processing such as a camera shake correction function, image processing such as camera shake correction cannot be performed on the medical observation device. In this case, it is necessary to perform image processing such as camera shake correction and rotation correction on the image output from the medical observation device at a later time. Here, images output from an image processing device such as the surgical information processing apparatus often include superimposed additional information (OSD information) such as character information indicating a setting or an alert regarding the image processing device. Therefore, applying image processing such as camera shake correction or rotation correction on such an image would apply the image processing also on the additional information, causing a problem of decreased visibility of the additional information, or distracted attention in the practitioner by the additional information.

For example, in a case where camera shake correction is performed in the endoscope device on an endoscopic image such as the surgical image IM2 illustrated in FIG. 1, the camera shake correction is performed before additional information such as OSD information is superimposed, and therefore, the camera shake correction would not affect the additional information such as OSD information. However, when camera shake correction is applied on an output video image from the endoscope device, that is, applied on an image after additional information such as OSD information is superimposed, reduction of blurring of the surgical video image accompanies shaking or blurring of the additional information such as OSD information. This causes distraction to the eyes of the practitioner and deterioration of visibility in reading additional information such as OSD information.

For example, a technique for correcting and stabilizing blurring of a surgical image for a surgical endoscope is disclosed in the following literature.

WO 2017/169139 A

When the above technology is applied to an image on which graphics such as an OSD and a graphical user interface (GUI), a computed tomography (CT) image and the like are superimposed, the result would be stabilization of the region of the surgical image but this accompanies shaking or blurring of the region with superimposed graphics, leading to discomfort for the user. In addition, since application of a blur correction technology causes shaking or blurring of the end of the corrected image or the end of the endoscopic mask which is uncomfortable for the user, it is a common practice to use an electronic mask to erase the region of the end of the image or the end of the endoscopic mask. In this case, in a case where graphics information is superimposed on the end of the image or the end of the endoscope mask, the superimposition region might totally or partially disappear by the electronic mask.

On the other hand, in a case where it is determined that additional information is attached, the surgical information processing apparatus 100 does not perform the first image processing. In the example of FIG. 1, the surgical information processing apparatus 100 executes second image processing of performing camera shake correction only for the region AR1 of the surgical image IM2. With this configuration, the surgical information processing apparatus 100 can suppress a situation in which additional information such as OSD information becomes the target of the camera shake correction and is blurred by this correction, which causes distraction of the practitioner's attention by the additional information or deterioration in visibility in reading the additional information such as the OSD information. Therefore, the surgical information processing apparatus 100 can perform image processing on a surgical video image without reducing the visibility of information such as OSD information or reducing the attention of the practitioner to the surgical video image. Therefore, the surgical information processing apparatus 100 can improve efficiency of surgery.

Furthermore, as described above, a surgical information processing system 1 performs image processing in consideration of additional information such as OSD information when performing image processing not on the medical observation device 10 side but in a configuration (surgical information processing apparatus 100) at a subsequent stage of the medical observation device 10. Therefore, the surgical information processing system 1 can perform image processing without providing a new device in the medical observation device 10. Therefore, the surgical information processing system 1 can improve the efficiency of the surgery without changing the existing medical observation device 10.

The above-described surgical information processing system 1 is targeted for surgical moving images such as images of surgical endoscopic operation, robotic operation, and video microscopic operation, for example. The surgical information processing system 1 determines whether the image is a surgical moving image (surgical image) such as an image of surgical endoscopic operation, robotic operation and video microscopic operation. The surgical information processing system 1 detects a region superimposed on an image on which graphics such as an OSD and a GUI, a CT image, and the like are superimposed. The surgical information processing system 1 notifies the user of the presence or absence of a superimposition region. The surgical information processing system 1 determines whether to or not to execute image processing or determines whether to partially execute image processing according to the information as to whether the image is a surgical image and the presence or absence of a superimposition region, and then, generates an image processing control signal instructing the execution or the partial execution of image processing. The surgical information processing system 1 executes/stops or partially executes image processing based on the image processing control signal. The surgical information processing system 1 executes image processing such as blur correction, electronic zoom, image rotation processing, PinP processing, and image enhancement. In the surgical information processing system 1, the user can instruct execution or stop of image processing via a user interface (IF). Regarding an image on which the graphics such as the OSD and the GUI, the CT image, and the like are superimposed, the surgical information processing system 1 refers to the history of a superimposition region including a superimposed image manually stopped by the user in the past, and stops image processing only on the superimposition region including the superimposed image manually stopped in the past. Note that details of these points will be described below.

As described above, the surgical information processing system 1 detects the presence or absence of the region in the image to which graphics such as the OSD and the GUI, the CT image and the like are superimposed, and automatically stops or partially stops the image processing, thereby solving the problem of movement of the superimposition region or disappearance of the superimposition region due to the image processing, leading to reduction of the discomfort in the user. In addition, the surgical information processing system 1 detects the presence or absence of the region in an image to which graphics such as an OSD and a GUI, a CT image and the like are superimposed, and notifies the user of the presence or absence of the region, thereby urging the user to stop image processing. In addition, the surgical information processing system 1 causes the user to manually stop the image processing upon receiving the notification, thereby reducing the discomfort in the user.

1-1-2. Other Determination Examples

The determination processing regarding the presence or absence of additional information is not limited to the above, and may be performed by appropriately using various types of information. This point will be described in detail below. For example, the surgical information processing apparatus 100 may determine whether additional information is attached to a surgical image based on metadata of the surgical image. The surgical information processing apparatus 100 may determine whether additional information is attached to a surgical image based on connected device information indicating the device connected to the surgical information processing apparatus 100. The surgical information processing apparatus 100 may determine whether additional information is attached to the surgical image based on the connected device information indicating the medical observation device 10 connected to the surgical information processing apparatus 100 as a transmission source that transmits images to the surgical information processing apparatus 100. For example, the surgical information processing apparatus 100 may determine whether additional information is attached to a surgical image based on information regarding digital imaging and communications in medicine (DICOM) of the surgical image. The surgical information processing apparatus 100 may determine whether additional information is attached to the surgical image based on information indicating the medical observation device 10 that has captured an image included in the information regarding DICOM. For example, in a case where the medical observation device 10 is a device on which the additional information is attached, the surgical information processing apparatus 100 may determine that the additional information is attached to the surgical image.

The surgical information processing apparatus 100 may determine whether additional information is attached to a surgical image based on a result of image analysis on the surgical image. The surgical information processing apparatus 100 may determine whether additional information is attached to the surgical image by analyzing the image by a technique such as image analysis. In a case where it is possible to obtain, by the image analysis on a surgical image, a result that character information or the like is included in the surgical image, the surgical information processing apparatus 100 may determine that additional information is attached to the surgical image.

The surgical information processing apparatus 100 may determine whether additional information is attached to the surgical image based on user setting information indicating the setting made by the user. The surgical information processing apparatus 100 may determine whether additional information is attached to the surgical image based on the setting of a practitioner who performs the surgery. The surgical information processing apparatus 100 may determine that additional information is not attached to the surgical image in a case where the practitioner performing the surgery has made the setting not to attach additional information. The surgical information processing apparatus 100 may determine that additional information is attached to a surgical image in a case where the practitioner performing the surgery has made the setting to attach the additional information.

Furthermore, the surgical information processing apparatus 100 may determine whether to perform the first image processing according to the user's selection. For example, even when additional information is attached to a surgical image, the surgical information processing apparatus 100 may determine to perform the first image processing in a case where the user selects to perform the first image processing. Even when additional information is not attached to a surgical image, the surgical information processing apparatus 100 may determine not to perform the first image processing in a case where the user selects not to perform the first image processing. For example, the surgical information processing apparatus 100 may determine whether to erase OSD information according to the type of the OSD information. For example, in a case where the user selects to hide OSD information of the type "icon", the surgical information processing apparatus 100 may perform processing of erasing the OSD information of the type "icon".

The surgical information processing apparatus 100 may make a determination by changing a threshold according to a device that has captured a surgical image. For example, the surgical information processing apparatus 100 may make a determination by changing a threshold according to the type of the medical observation device 10. For example, the surgical information processing apparatus 100 may determine whether additional information is attached by using a threshold corresponding to each type of the medical observation device 10. For example, in a case where the type of the medical observation device 10 that has captured a surgical image is "endoscope", the surgical information processing apparatus 100 may determine whether additional information is attached by using a threshold corresponding to the type "endoscope". For example, in a case where the type of the medical observation device 10 that has captured a surgical image is "microscope", the surgical information processing apparatus 100 may determine whether additional information is attached by using a threshold corresponding to the type "microscope".

The surgical information processing apparatus 100 may perform processing using thresholds at a plurality of levels. For example, the surgical information processing apparatus 100 may determine not to perform image processing on a pixel whose integrated value of differences is smaller than a first level threshold that is a lowest threshold. The surgical information processing apparatus 100 may determine to perform processing of filling pixels (pixel filling) regarding a pixel of a predetermined color or luminance value (also referred to as "luminance") in pixels whose integrated value of differences is smaller than a second level threshold larger than the first level threshold. The surgical information processing apparatus 100 may determine to perform pixel filling of filling pixels of the color and luminance of the original pixels regarding a pixel in which the integrated value of the differences is smaller than the second level threshold. The surgical information processing apparatus 100 may determine to perform image processing on a pixel having an integrated value of differences being the second level threshold or more. In addition, the surgical information processing apparatus 100 may determine transmission of additional information attached to the surgical image. The surgical information processing apparatus 100 may determine whether additional information attached to a surgical image has transparency by using a plurality of levels of thresholds. In this case, the surgical information processing apparatus 100 may determine a pixel having an integrated value of differences smaller than a first level threshold as additional information having no transparency. The surgical information processing apparatus 100 may determine a pixel having an integrated value of differences being the first level threshold or more and smaller than the second level threshold as additional information having transparency. The surgical information processing apparatus 100 may determine that a pixel having an integrated value of differences being the second level threshold or more is not the additional information. For example, the surgical information processing apparatus 100 may determine a pixel having an integrated value of differences being the second level threshold or more as a pixel corresponding to a surgical image. Note that the above is an example, and the surgical information processing apparatus 100 may determine whether additional information is attached to a surgical image by appropriately using various types of information.

[1-2. Configuration of Surgical Information Processing System According to First Embodiment]

The surgical information processing system 1 illustrated in FIG. 2 will be described. As illustrated in FIG. 2, the surgical information processing system 1 includes a medical observation device 10, an image reception device 50, and a surgical information processing apparatus 100. The medical observation device 10, the image reception device 50, and the surgical information processing apparatus 100 are communicably connected with each other in a wired or wireless connection via a predetermined communication network (such as a network N in FIG. 3). FIG. 2 is a diagram illustrating a configuration example of a surgical information processing system according to the first embodiment. Note that the surgical information processing system 1 illustrated in FIG. 2 may include a plurality of medical observation devices 10, a plurality of image reception devices 50, and a plurality of surgical information processing apparatuses 100. For example, the surgical information processing system 1 also functions as a transmission system that actualizes transmission of information between individual devices.

The medical observation device 10, also referred to as a modality, is a device used for medical purposes. The medical observation device 10 includes an imaging unit such as an image sensor and has an imaging function. The medical observation device 10 captures an image of an imaging target such as a living tissue and generates a medical image. The medical observation device 10 images not only a living tissue but also various objects. For example, the medical observation device 10 captures an image of a site as a target of operation and generates a surgical image. For example, the medical observation device 10 is a medical device such as an operative field camera, an endoscope, or a microscope. The medical observation device 10 is not limited to an operative field camera, an endoscope, a microscope, or the like, and may be any device having a function of capturing an image, not limited to a specific configuration.

The image reception device 50 is a device that receives images from various external devices. The image reception device 50 is a device that displays and records images received from various external devices. The image reception device 50 is a device (image management server) such as a display device that displays an image and a storage device that records an image. Examples of the image reception device 50 include a monitor (display) or a projector used is a display device, a recorder used as a storage device, and the like. The image reception device 50 receives an image output from the surgical information processing apparatus 100. The image reception device 50 receives an image transmitted from the surgical information processing apparatus 100.

The surgical information processing apparatus 100 is an information processing apparatus (computer) that performs image processing on an image. The surgical information processing apparatus 100 executes image processing on an image acquired from an external device, and transmits the image that has undergone the image processing to another external device.

The surgical information processing apparatus 100 executes image processing described below on a medical image such as a surgical image acquired from the medical observation device 10. The surgical information processing apparatus 100 outputs the medical image that has undergone the image processing to the image reception device 50.

The surgical information processing apparatus 100 may be any type of apparatus as long as it can perform image processing such as camera shake correction and rotation correction on an image such as a surgical image. For example, the surgical information processing apparatus 100 may be an interlace/progressive (IP) converter that converts an electrical signal of an image into an optical signal. The surgical information processing apparatus 100 performs image processing such as camera shake correction and rotation correction by appropriately using various techniques. For example, in performing camera shake correction, the surgical information processing apparatus 100 may correct the camera shake by executing motion vector extraction processing on a surgical image and then moving the surgical image in an opposite phase with respect to the extracted motion vector. For example, in a case where the additional information is attached, the surgical information processing apparatus 100 may correct camera shake by executing processing of extracting a motion vector on a surgical region of the surgical image and then moving the surgical region in an opposite phase with respect to the extracted motion vector.

The surgical information processing apparatus 100 determines whether additional information is attached to a surgical image, performs first image processing in a case where it is determined that additional information is not attached, and does not perform the first image processing in a case where it is determined that additional information is attached. The surgical information processing apparatus 100 determines whether the image is a surgical image. The surgical information processing apparatus 100 determines whether the image acquired from the medical observation device 10 is a surgical image. In a case where the image is a surgical image, the surgical information processing apparatus 100 determines whether additional information is attached to the image. The surgical information processing apparatus 100 performs the first image processing in a case where it is determined that additional information is not attached, and does not perform the first image processing in a case where it is determined that additional information is attached.

[1-3. Configuration of Surgical Information Processing Apparatus According to First Embodiment]

Figure 3:
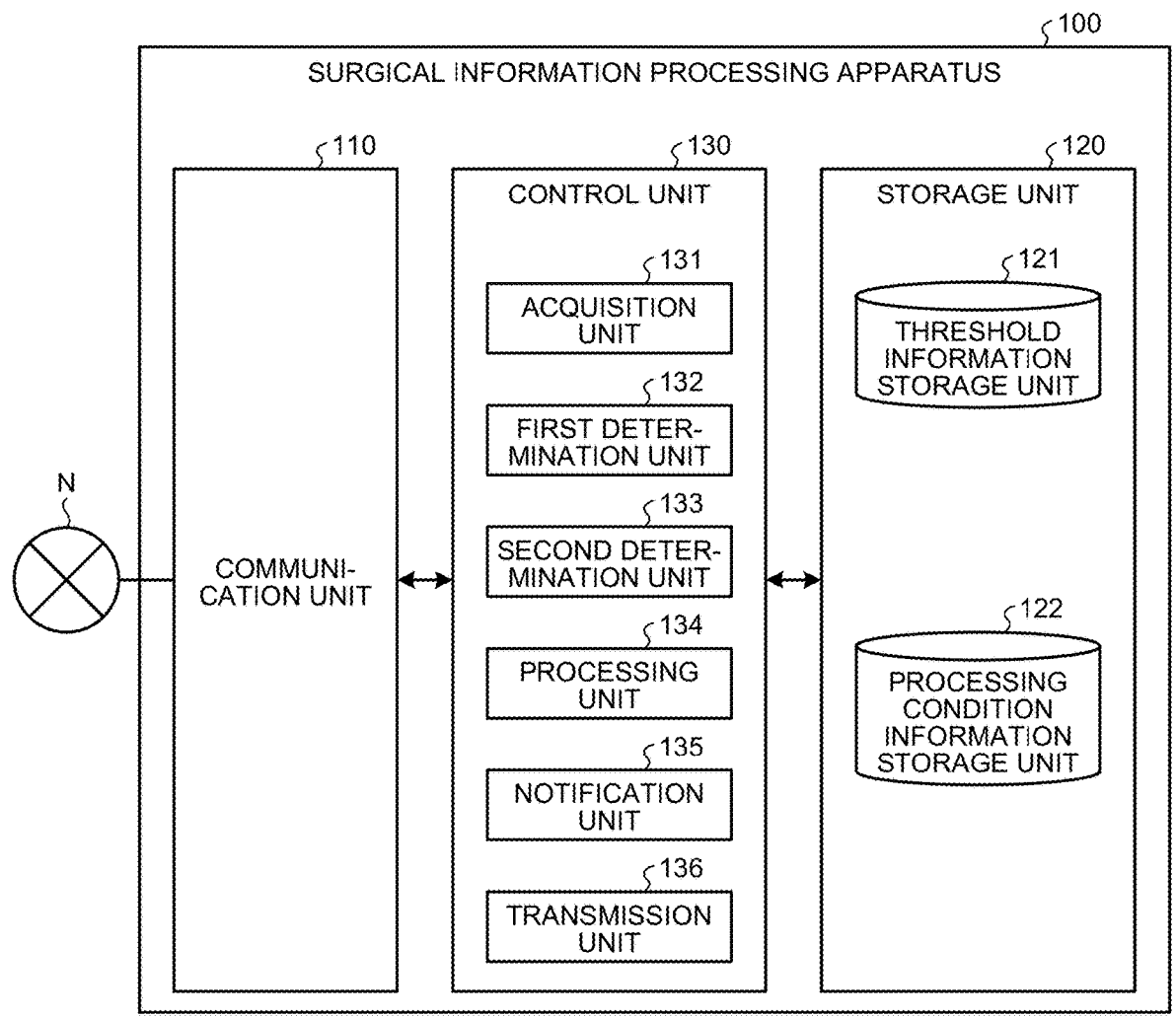
FIG. 3 is a diagram illustrating a configuration example of a surgical information processing apparatus according to the first embodiment.

Next, a configuration of the surgical information processing apparatus 100 as an example of a surgical information processing apparatus that executes information processing according to the first embodiment will be described. FIG. 3 is a diagram illustrating a configuration example of the surgical information processing apparatus 100 according to the first embodiment.

As illustrated in FIG. 3, the surgical information processing apparatus 100 includes a communication unit 110, a storage unit 120, and a control unit 130. The surgical information processing apparatus 100 may include an input unit (for example, a keyboard, a mouse, etc.) that receives various operations from an administrator or the like of the surgical information processing apparatus 100, and a display unit (for example, a liquid crystal display, etc.) for displaying various types of information.

The communication unit 110 is actualized by a network interface card (NIC), for example. The communication unit 110 is connected to the network N in a wired or wireless connection, and transmits and receives information to and from other information processing apparatuses (computers) such as the medical observation device 10 and the image reception device 50. Furthermore, the communication unit 110 may transmit and receive information to and from a user terminal (not illustrated) used by the user.

The storage unit 120 is implemented by semiconductor memory elements such as random access memory (RAN) and flash memory, or other storage devices such as a hard disk or an optical disc. As illustrated in FIG. 3, the storage unit 120 according to the first embodiment includes a threshold information storage unit 121 and a processing condition information storage unit 122. Although not illustrated, the storage unit 120 stores various types of information in addition to the information illustrated in the threshold information storage unit 121 and the processing condition information storage unit 122. The storage unit 120 stores various types of information for performing image processing. For example, the storage unit 120 stores information indicating specific processing performed as the first image processing and specific processing performed as the second image processing. For example, the storage unit 120 stores a program for executing the first image processing (first image processing program) and a program for executing the second image processing (second image processing program).

Figure 4:
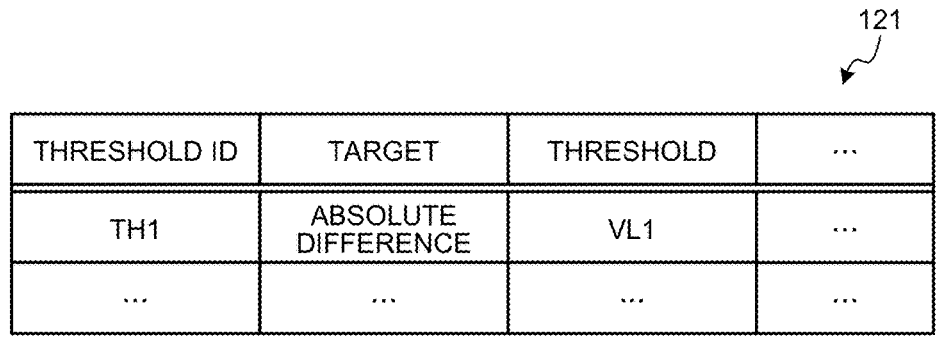
FIG. 4 is a diagram illustrating an example of a threshold information storage unit according to the first embodiment.

The threshold information storage unit 121 according to the first embodiment stores various types of information related to thresholds. The threshold information storage unit 121 stores various types of information related to thresholds used for various determinations. FIG. 4 is a diagram illustrating an example of a threshold information storage unit according to the first embodiment. The threshold information storage unit 121 illustrated in FIG. 4 includes items such as "Threshold ID", "Target", and "Threshold".

"Threshold ID" indicates identification information for identifying the threshold. "Target" indicates a target to which the threshold is applied. "Threshold" indicates a specific value of the threshold identified by the corresponding threshold ID.

In the example of FIG. 4, the threshold (threshold TH1) identified by the threshold ID "TH1" indicates that the target is "Absolute difference". That is, the threshold TH1 indicates that the threshold TH1 is used for comparison with the absolute difference. In this case, the threshold TH1 indicates a value used for comparison with the absolute difference, and a value used for determination of the presence or absence of additional information. The value of the threshold TH1 indicates "VL1". In the example of FIG. 4, the threshold TH1 is indicated by an abstract code such as "VL1", but the value of the threshold TH1 is a specific numerical value in practice.

Note that the threshold information storage unit 121 is not limited to the above, and may store various types of information depending on the purpose.

Figure 5:
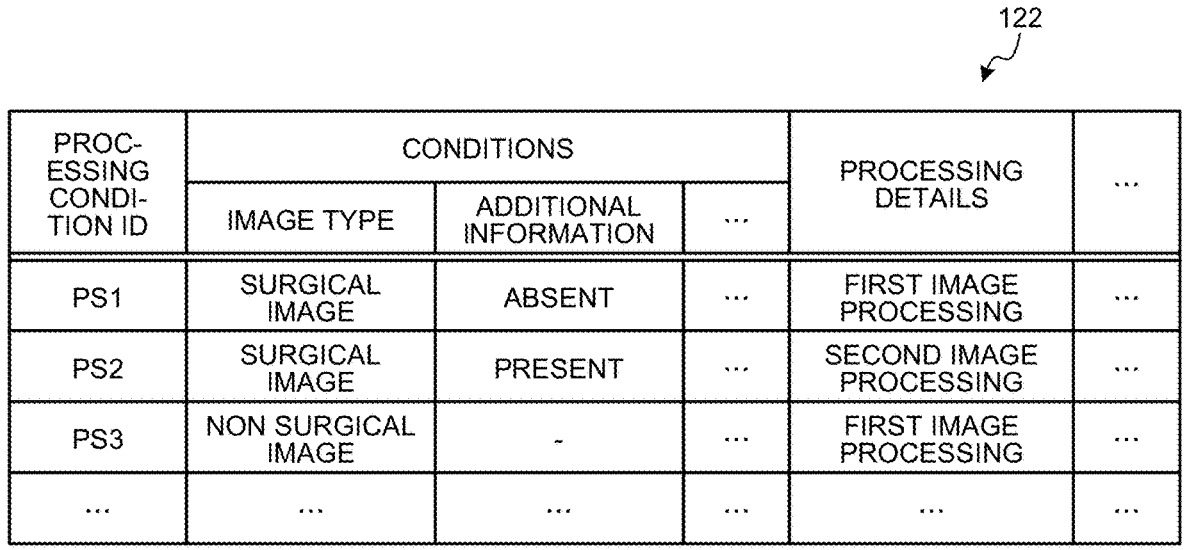
FIG. 5 is a diagram illustrating an example of a processing condition information storage unit according to the first embodiment.

The processing condition information storage unit 122 according to the first embodiment stores various types of information regarding the processing condition. The processing condition information storage unit 122 stores various types of information regarding combinations of various types of conditions and image processing performed when the conditions are satisfied. FIG. 5 is a diagram illustrating an example of a processing condition information storage unit according to the first embodiment. The processing condition information storage unit 122 illustrated in FIG. 5 includes items such as "Processing condition ID", "Condition", and "Processing details".

"Processing condition ID" indicates identification information for identifying a processing condition. "Condition" indicates a condition identified by Processing condition ID. "Condition" includes items such as "image type" and "additional information". Note that "Condition" is not limited to only "Image type" or "Additional information", and may include any item that can be a condition. "Processing details" indicates specific processing performed in a case where a condition identified by Processing condition ID is satisfied.

In the example of FIG. 5, the processing condition (Processing condition PS1) identified by Processing condition ID "PS1" includes conditions that the image type is "Surgical image" and the additional information is "Absent". This also indicates that the processing executed when the processing condition PS1 is satisfied is the first image processing. That is, it is indicated that the first image processing is executed on an image under the condition that the image type is "Surgical image" and the additional information is "none".

The example also indicates that the processing condition (Processing condition PS2) identified by Processing condition ID "PS2" includes conditions that the image type is "Surgical image" and the additional information is "Present". This example also indicates that the processing executed when the processing condition PS2 is satisfied is the second image processing. That is, it is indicated that the second image processing is executed on an image under the condition that the image type is "Surgical image" and the additional information is "Present".

In addition, the processing condition (Processing condition PS3) identified by Processing condition ID "PS3" includes conditions that the image type is "Non surgical image" and additional information is "blank (not to be a condition)". This also indicates that the processing executed when the processing condition PS3 is satisfied is the first image processing. That is, when the image type is "Non surgical image", the first image processing is executed regardless of the presence or absence of additional information. Note that, even when the image type is "Non surgical image", the surgical information processing apparatus 100 may switch between the first image processing and the second image processing according to the presence or absence of the additional information similarly to a case where the type is a surgical image.

Note that the above is an example, and the processing condition information storage unit 122 may store various types of information depending on the purpose, other than the above. When performing the second image processing, the processing condition information storage unit 122 may store information indicating which one of the first to fourth processing modes illustrated in FIGS. 15 to 18 is to be applied as the image processing to be performed. When additional information is to be attached to the surgical image, the processing condition information storage unit 122 may store information indicating which one of the first to fourth processing modes illustrated in FIGS. 15 to 18 is to be applied as the image processing to be performed. In addition, the processing condition information storage unit 122 may store various processing conditions in addition to the processing conditions PS1 to PS3.

Returning to FIG. 3, and description will continue. The control unit 130 is actualized by execution of programs stored in the surgical information processing apparatus 100 (for example, information processing program such as a surgical information processing program according to the present disclosure) by a central processing unit (CPU), a micro processing unit (MPU), or the like, using random access memory (RAN) or the like, as a working area. Furthermore, the control unit 130 is actualized by, for example, an integrated circuit such as an application specific integrated circuit (ASIC) or a field programmable gate array (FPGA).

As illustrated in FIG. 3, the control unit 130 includes an acquisition unit 131, a first determination unit 132, a second determination unit 133, a processing unit 134, a notification unit 135, and a transmission unit 136, and actualizes or executes information processing functions and effects described below. The internal configuration of the control unit 130 is not limited to the configuration illustrated in FIG. 3, and may be another configuration as long as it is a configuration that performs information processing described below. Furthermore, the connection relationship of the processing units included in the control unit 130 is not limited to the connection relationship illustrated in FIG. 3, and may be a different connection relationship.

The acquisition unit 131 acquires various types of information. The acquisition unit 131 acquires various types of information from an external information processing apparatus. The acquisition unit 131 acquires various types of information from the medical observation device 10 and the image reception device 50.

The acquisition unit 131 acquires various types of information from the storage unit 120. The acquisition unit 131 acquires various types of information from the threshold information storage unit 121 and the processing condition information storage unit 122.

The acquisition unit 131 acquires a surgical image. The acquisition unit 131 acquires a surgical image from the medical observation device. The acquisition unit 131 acquires metadata of the surgical image. The acquisition unit 131 acquires metadata including information regarding DICOM of a surgical image. The acquisition unit 131 acquires user setting information indicating setting made by the user. The acquisition unit 131 acquires connected device information indicating a device connected to the surgical information processing apparatus.

The acquisition unit 131 acquires a plurality of surgical images including the surgical image. The acquisition unit 131 acquires information indicating a target region that displays additional information corresponding to a device that has captured the surgical image. The acquisition unit 131 acquires a first threshold that is a threshold for difference and a second threshold that is a threshold for luminance.

The acquisition unit 131 acquires various types of information analyzed by the first determination unit 132. The acquisition unit 131 acquires various types of information generated by the second determination unit 133. The acquisition unit 131 acquires various types of information generated by the second determination unit 133. The acquisition unit 131 acquires various types of information processed by the processing unit 134.

The acquisition unit 131 acquires first information to be a trigger for an interaction, second information indicating a response to the first information, and third information indicating a reaction to the second information. The acquisition unit 131 acquires first information that is a question, second information that is a reply to the first information, and third information that is a reply to the second information. The acquisition unit 131 acquires first information corresponding to an utterance of a first entity, second information corresponding to an utterance of a second entity, and third information corresponding to an utterance of a third entity. The acquisition unit 131 acquires first information, second information corresponding to an utterance of a second entity different from the first entity, and third information corresponding to an utterance of a third entity that is the first entity.

The acquisition unit 131 acquires first information corresponding to an utterance of a first entity that is an agent of an interaction system, second information corresponding to an utterance of a second entity that is a user, and third information corresponding to an utterance of a third entity that is an agent of the interaction system. The acquisition unit 131 acquires first information, second information, and third information, at least one of the first information, the second information, and the third information has been input by the user. The acquisition unit 131 acquires the first information presented to the input user, the second information input by the input user, and the third information input by the input user. The acquisition unit 131 acquires meta information regarding the input user.

The acquisition unit 131 acquires a plurality of pieces of unit information that is information regarding a constituent unit of an interaction corresponding to a combination of first information to be a trigger for an interaction, second information indicating a response to the first information, and third information indicating a reaction to the second information. The acquisition unit 131 acquires a plurality of pieces of unit information regarding a constituent unit that is a combination of the first information, the second information, and the third information. The acquisition unit 131 acquires connection method designation information between combinations by the user to which a plurality of pieces of unit information are presented. The acquisition unit 131 acquires connection information that is information connecting combinations of the first information, the second information, and the third information. The acquisition unit 131 acquires the connection information designated by the user. The acquisition unit 131 acquires a plurality of pieces of unit information regarding the constituent unit that is each of the first information, the second information, and the third information.

In the example of FIG. 1, the acquisition unit 131 acquires a surgical image IM1. The acquisition unit 131 acquires a surgical image IM2.

The first determination unit 132 makes a determination on various types of information. The first determination unit 132 makes a determination on various types of information based on information from an external information processing apparatus. The first determination unit 132 makes a determination on various types of information based on information from other information processing apparatuses such as the medical observation device 10 and the image reception device 50. The first determination unit 132 determines various types of information based on the information stored in the threshold information storage unit 121 or the processing condition information storage unit 122. The first determination unit 132 makes a determination on various types of information based on the information acquired by the acquisition unit 131.

The first determination unit 132 makes a determination on various types of information based on various types of information acquired by the acquisition unit 131. The first determination unit 132 determines whether the image is a surgical image. The first determination unit 132 analyzes the image to determine whether the image is a surgical image.

The second determination unit 133 makes a determination on various types of information. The second determination unit 133 makes a determination on various types of information based on information from an external information processing apparatus or information stored in the storage unit 120. The second determination unit 133 makes a determination on various types of information based on information from other information processing apparatuses such as the medical observation device 10 and the image reception device 50. The second determination unit 133 determines various types of information based on the information stored in the threshold information storage unit 121 or the processing condition information storage unit 122. The second determination unit 133 makes a determination on various types of information based on the information acquired by the acquisition unit 131.

The second determination unit 133 makes a determination on various types of information based on various types of information acquired by the acquisition unit 131. The second determination unit 133 makes a determination on various types of information based on the various types of information determined by the first determination unit 132. The second determination unit 133 makes a determination on various types of information based on a result of determination obtained by the first determination unit 132. Note that the first determination unit 132 and the second determination unit 133 may be an integrated determination unit.

The second determination unit 133 determines whether additional information is attached to a surgical image acquired by the acquisition unit 131. The second determination unit 133 determines whether additional information is attached to the surgical image based on metadata acquired by the acquisition unit 131. The second determination unit 133 determines whether additional information is attached to the surgical image based on the result of the image analysis on the surgical image. The second determination unit 133 determines whether additional information is attached to the surgical image based on the result of the image analysis regarding the color of the surgical image. The second determination unit 133 determines whether additional information is attached to a surgical image based on a result of image analysis of the surgical image using machine learning.

The second determination unit 133 determines whether additional information is attached to the surgical image based on the user setting information acquired by the acquisition unit 131. The second determination unit 133 determines whether additional information is attached to the surgical image based on the connected device information acquired by the acquisition unit 131.

The second determination unit 133 makes a determination on a region of the additional information attached to the surgical image. The second determination unit 133 makes a determination on a region of the additional information to be attached to the surgical image corresponding to zoom processing. The second determination unit 133 makes a determination on a region of additional information that is a frozen image to be attached to the surgical image. The second determination unit 133 makes a determination on a region of additional information that is character information to be attached to the surgical image. The second determination unit 133 makes a determination on a region in which character information to be attached to the surgical image is arranged. The second determination unit 133 makes a determination on a region of additional information which is a frame to be attached to the surgical image. The second determination unit 133 makes a determination on a region of a frame to be attached to the surgical image. The second determination unit 133 makes a determination on a region of a frame arranged at an end of the surgical image. The second determination unit 133 makes a determination on a region of a frame surrounding peripheral ends of the surgical image. The second determination unit 133 determines a mask to be applied to the surgical image. The second determination unit 133 determines a mask to be arranged at peripheral ends of the surgical image. The second determination unit 133 makes a determination on a region of additional information having transparency to be attached to the surgical image. The second determination unit 133 makes a determination on transmission of the additional information attached to the surgical image. The second determination unit 133 makes a determination on transmission of the additional information attached to the surgical image.

The second determination unit 133 determines whether additional information is attached to the surgical image by comparing a plurality of surgical images. The second determination unit 133 determines whether additional information is attached to the surgical image based on the comparison of the colors of the plurality of surgical images. The second determination unit 133 determines a portion in which the difference between the pixel values of the plurality of surgical images does not exceed a threshold as additional information. The second determination unit 133 makes a determination by changing the threshold according to the device that has captured the surgical image.

When a plurality of surgical images including a special light image and an observation light image have been acquired, the second determination unit 133 determines whether additional information is attached by making a comparison using the observation light image. In a case where a plurality of surgical images including a special light image that is an infrared (IR) light image and an observation light image that is a visible light image are acquired, the second determination unit 133 determines whether additional information is attached by making a comparison using the observation light image.

The second determination unit 133 makes a determination regarding additional information based on a comparison between a first threshold and a summed value of the absolute differences of a plurality of surgical images and a comparison between a second threshold and a summed value of the luminance values of the plurality of surgical images. The second determination unit 133 discriminates between a mask image and OSD information based on a comparison between the first threshold and the summed value of the absolute differences of the plurality of surgical images and a comparison between the second threshold and the summed value of the luminance values of the plurality of surgical images. The second determination unit 133 makes a determination on the additional information by defining the summed value of the absolute differences of the plurality of surgical images as a first axis and the summed value of the luminance values of the plurality of surgical images as a second axis.

In the example of FIG. 1, the second determination unit 133 determines that additional information is not attached to the surgical image IM1. The second determination unit 133 determines that additional information is attached to the surgical image IM2.

The processing unit 134 executes various types of information processing. The processing unit 134 performs various types of image processing. For example, the processing unit 134 executes various types of information processing based on information from an external information processing apparatus or information stored in the storage unit 120. The processing unit 134 executes various types of information processing based on information from other information processing apparatuses such as the medical observation device 10 and the image reception device 50. The processing unit 134 executes various types of information processing based on the information stored in the threshold information storage unit 121 or the processing condition information storage unit 122.

The processing unit 134 executes various types of information processing based on the various types of information acquired by the acquisition unit 131. The processing unit 134 executes various types of information processing based on the various types of information determined by the first determination unit 132. The processing unit 134 executes various types of information processing based on the result of determination obtained by the first determination unit 132. The processing unit 134 executes various types of information processing based on the various types of information determined by the second determination unit 133. The processing unit 134 executes various types of information processing based on the result of determination obtained by the second determination unit 133.

The processing unit 134 performs analysis processing on an image. The processing unit 134 performs various types of processing related to image processing. The processing unit 134 performs processing on the image information (image) acquired by the acquisition unit 131. The processing unit 134 performs processing on an image by appropriately using a technology related to image processing.

The processing unit 134 performs the first image processing when it is determined that additional information is not attached, and does not perform the first image processing when it is determined that the additional information is attached, based on the determination of the second determination unit 133. In a case where it is determined that additional information is attached, the second image processing different from the first image processing is performed. The processing unit 134 performs first image processing that is image processing targeted for an entire portion of the surgical image. The processing unit 134 performs second image processing including image processing of a type same as the type of the first image processing, the processing being targeted for a region of the surgical image other than an additional information region corresponding to the additional information. The processing unit 134 performs second image processing including image processing of a type different from the type of the first image processing, the processing being targeted for the additional information region.

The processing unit 134 performs second image processing including pixel filling processing targeted for the additional information region. The processing unit 134 performs first image processing including at least one of zoom, camera shake correction, rotation correction, or picture in picture (PinP).

Note that the processing unit 134 may use any technique to execute image processing as long as desired image processing can be executed, and thus executes image processing using various image processing techniques as appropriate. The processing unit 134 may execute image processing by appropriately using various types of information. The processing unit 134 performs various types of image processing on an image signal such as RAW data acquired from the medical observation device 10, for example. Examples of the image processing include various known signal processing such as development processing, high image quality processing (band enhancement processing, super-resolution processing, noise reduction (NR) processing, camera shake correction processing, and/or the like), and/or enlargement processing (electronic zoom processing). Furthermore, the processing unit 134 performs demodulation processing on the image signals for performing AE, AF, and AWB.

In the example of FIG. 1, the processing unit 134 executes first image processing on the image IM1. The processing unit 134 executes first image processing on the image IM1 to generate the image IM10. In addition, the processing unit 134 executes second image processing on the image IM2. The processing unit 134 executes second image processing on the image IM2 to generate the image IM20.

The notification unit 135 notifies information. The notification unit 135 notifies the user of information. The notification unit 135 notifies (transmits) information to a terminal device or the like used by the user. In a case where the surgical information processing apparatus 100 includes an output unit such as a display (display screen) or a speaker, the notification unit 135 may notify the user of information by the output unit.

The notification unit 135 notifies various types of information based on the various types of information acquired by the acquisition unit 131. The notification unit 135 notifies various types of information based on various types of information collected by the first determination unit 132. The notification unit 135 notifies various types of information based on the result of determination made by the first determination unit 132. The notification unit 135 notifies various types of information based on various types of information generated by the second determination unit 133. The notification unit 135 notifies various types of information based on the result of determination made by the second determination unit 133. The notification unit 135 notifies various types of information based on the various types of information processed by the processing unit 134.

The transmission unit 136 provides various types of information to an external information processing apparatus. The transmission unit 136 transmits various types of information to an external information processing apparatus. For example, the transmission unit 136 transmits various types of information to other information processing apparatuses such as the medical observation device 10 and the image reception device 50. The transmission unit 136 provides the information stored in the storage unit 120. The transmission unit 136 transmits the information stored in the storage unit 120.

The transmission unit 136 provides various types of information based on information from other information processing apparatuses such as the medical observation device 10 and the image reception device 50. The transmission unit 136 provides various types of information based on the information stored in the storage unit 120. The transmission unit 136 provides various types of information based on the information stored in the threshold information storage unit 121 or the processing condition information storage unit 122.

In the example of FIG. 1, the transmission unit 136 transmits the images IM10 and IM20 which have undergone the image processing by the processing unit 134 to the image reception device 50.

[1-4. Procedure of Information Processing According to First Embodiment]

Next, various types of information processing procedures according to the first embodiment will be described with reference to FIG. 6.

Figure 6:
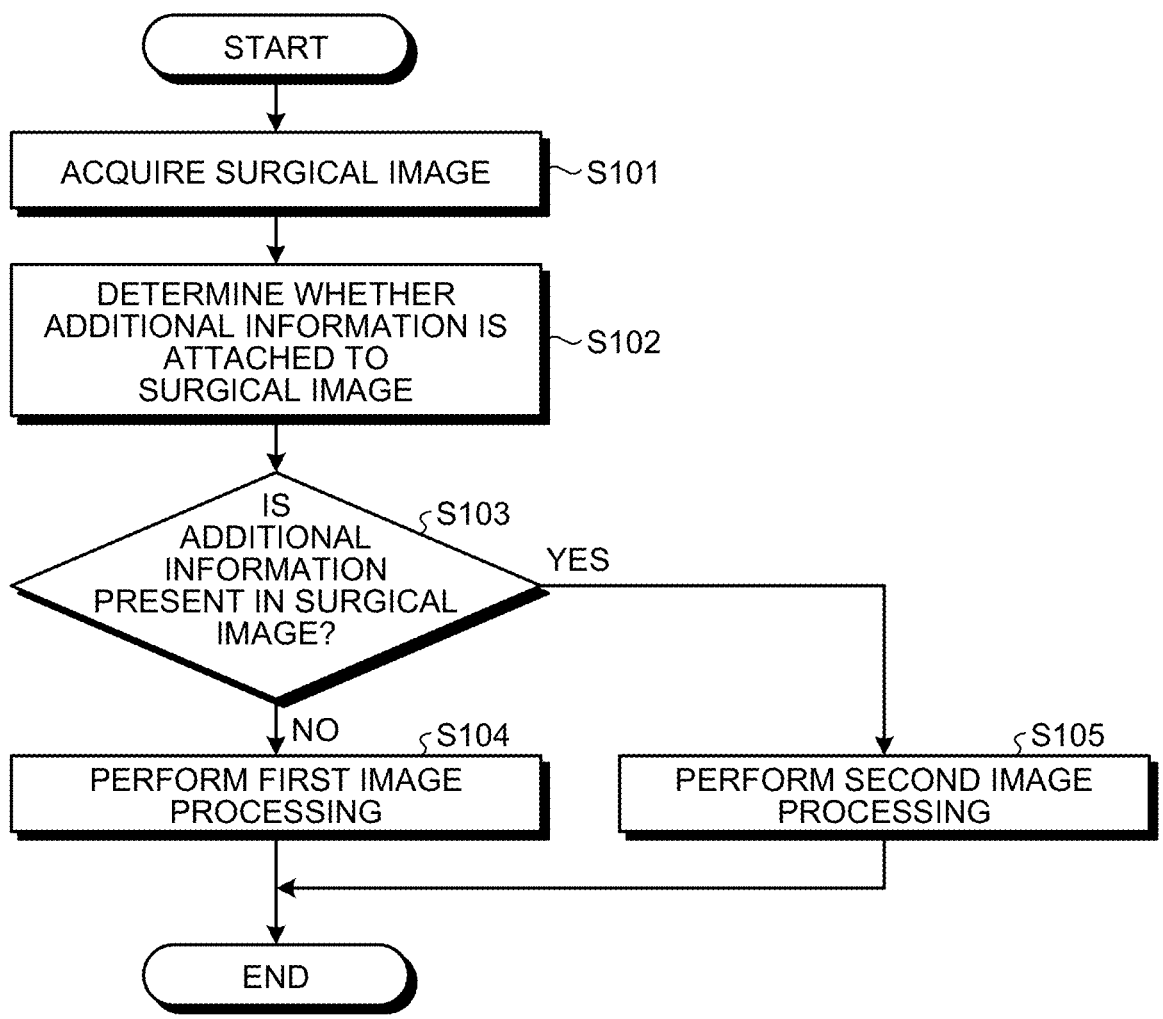
FIG. 6 is a flowchart illustrating a procedure of information processing according to the first embodiment.

FIG. 6 is a flowchart illustrating a procedure of information processing according to the first embodiment. Specifically, FIG. 6 is a flowchart illustrating a procedure of collection processing performed by the surgical information processing apparatus 100.

As illustrated in FIG. 6, the surgical information processing apparatus 100 acquires a surgical image (step S101). The surgical information processing apparatus 100 determines whether additional information is attached to the surgical image (step S102).

When there is no additional information in the surgical image (step S103: No), the surgical information processing apparatus 100 executes first image processing (step S104).

On the other hand, when the surgical image includes the additional information (step S103: Yes), the surgical information processing apparatus 100 executes second image processing (step S105). In a case where the surgical image includes additional information, the surgical information processing apparatus 100 executes the second image processing without executing the first image processing.

[1-5. Example of Specific Configuration of Surgical Information Processing System]

Figure 7:
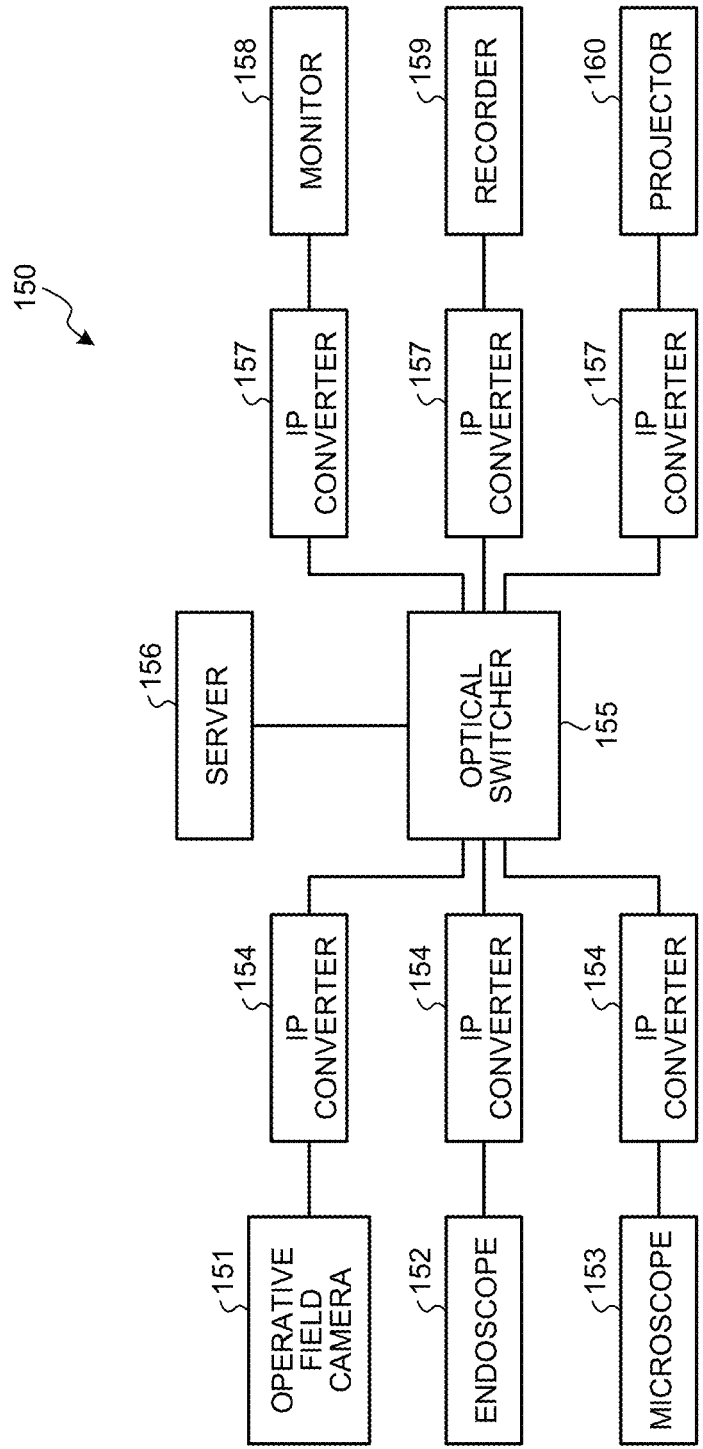
FIG. 7 is a schematic diagram illustrating a specific example of a surgical information processing system.

Next, a surgical information processing system 150 as a specific example of the surgical information processing system 1 will be described with reference to FIG. 7. FIG. 7 is a schematic diagram illustrating a specific example of a surgical information processing system.

The surgical information processing system 150 includes an operative field camera 151, an endoscope 152, a microscope 153, an IP converter 154, an optical switcher 155, a server 156, an IP converter 157, a monitor 158, a recorder 159, and a projector 160.

An electrical signal of a medical image individually captured by of the operative field camera 151, the endoscope 152, and the microscope 153 is converted into an optical signal by the IP converter 154, and is output to any of the IP converters 157 by the optical switcher 155.

The IP converter 157 converts the optical signal supplied from the optical switcher into an electrical signal and supplies the electrical signal to the monitor 158, the recorder 159, and the projector 160, individually. The server 156 instructs the optical switcher 155 regarding which of the IP converters 154 and the IP converters 157 are to be connected to the optical switcher 155. For example, the IP converter 154 or the IP converter 157 corresponds to the surgical information processing apparatus 100 illustrated in FIG. 2.

For example, the operative field camera 151, the endoscope 152, and the microscope 153 correspond to the medical observation device 10 illustrated in FIG. 2. In addition, the monitor 158, the recorder 159, and the projector 160 correspond to the image reception device 50 illustrated in FIG. 2. The image reception device 50 may be the server 156.

The surgical information processing apparatus 100 corresponds to at least one of the IP converter 154, the IP converter 157, and the server 156. Note that the server 156 may be omitted in FIG. 7, and in that case, the surgical information processing apparatus 100 corresponds to at least one of the IP converter 154 and the IP converter 157. For example, the IP converter 154 or the IP converter 157 which is the surgical information processing apparatus 100 acquires a surgical image from the operative field camera 151, the endoscope 152, or the microscope 153 which is the medical observation device 10, and transmits the surgical image that has undergone image processing according to the presence or absence of the additional information to the image reception device 50. Note that a specific configuration of the surgical information processing system 150 illustrated in FIG. 7 is an example of the surgical information processing system 1, and thus, the surgical information processing system 1 may take any form as long as the configuration illustrated in FIG. 2 is implemented.

[1-6. Conceptual Diagram of Functional Configuration Example of the Surgical Information Processing System]

Next, a functional configuration example of the surgical information processing system will be described with reference to FIGS. 8 to 13. Note that the functional configurations illustrated in FIGS. 8 to 13 are implemented by configurations of the surgical information processing apparatus 100, the medical observation device 10, and the like in the surgical information processing system 1.

[1-6-1. Assumable Field for Implementation of Surgical Information Processing System]

Figure 8:
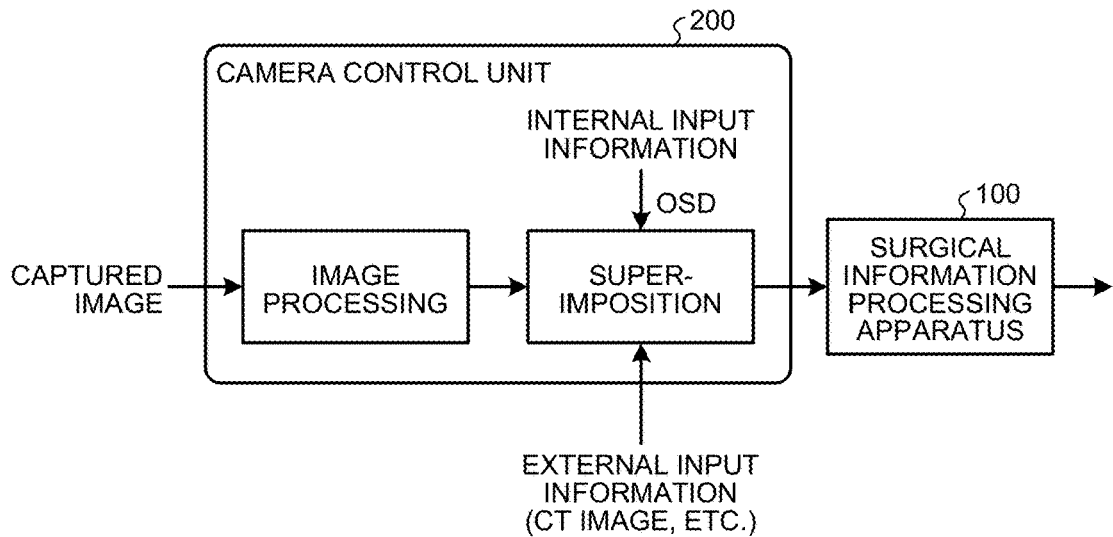
FIG. 8 is a diagram illustrating an example of a conceptual diagram of a functional configuration of a surgical information processing system.

First, an assumable field for implementation of the surgical information processing system will be described with reference to FIG. 8. FIG. 8 is a diagram illustrating an example of a conceptual diagram of a functional configuration of a surgical information processing system. Specifically, FIG. 8 is a diagram conceptually illustrating a flow of information in the surgical information processing system.

As illustrated in FIG. 8, the surgical information processing apparatus 100 acquires by the camera control unit 200 an image in which additional information such as OSD information is attached to a captured image. The camera control unit 200 is provided at a preceding stage of the surgical information processing apparatus 100, and attaches additional information such as OSD information to the captured image before the surgical information processing apparatus 100 performs processing on the image. The camera control unit 200 may be integrated with the medical observation device 10 or may be separate from the medical observation device 10.

As described above, the surgical information processing system 1 mainly targets surgical moving images (surgical images) such as images for surgical endoscopic operation, robotic operation, and video microscopic operation. The surgical information processing system 1 uses a non surgical image as an input image. In that case, however, image processing is applied to the entire screen without making determination of a superimposition region to be described below. As illustrated in FIG. 8, the surgical information processing apparatus 100 uses, as an input, an image obtained by performing image processing using the camera control unit 200 on a surgical image captured by a camera. The camera control unit 200 generates and outputs an image on which graphics such as an OSD and a GUI are superimposed or external input information such as a CT image captured beforehand is superimposed, in addition to image processing such as digital development and image quality improvement. Since image processing is performed by the surgical information processing apparatus 100 in the subsequent stage using the image from the camera control unit 200 as input, it is important to determine the presence or absence of the additional information as described above and switch the image processing according to the determination result.

[1-6-2. Surgical Information Processing Apparatus]

Figure 9:
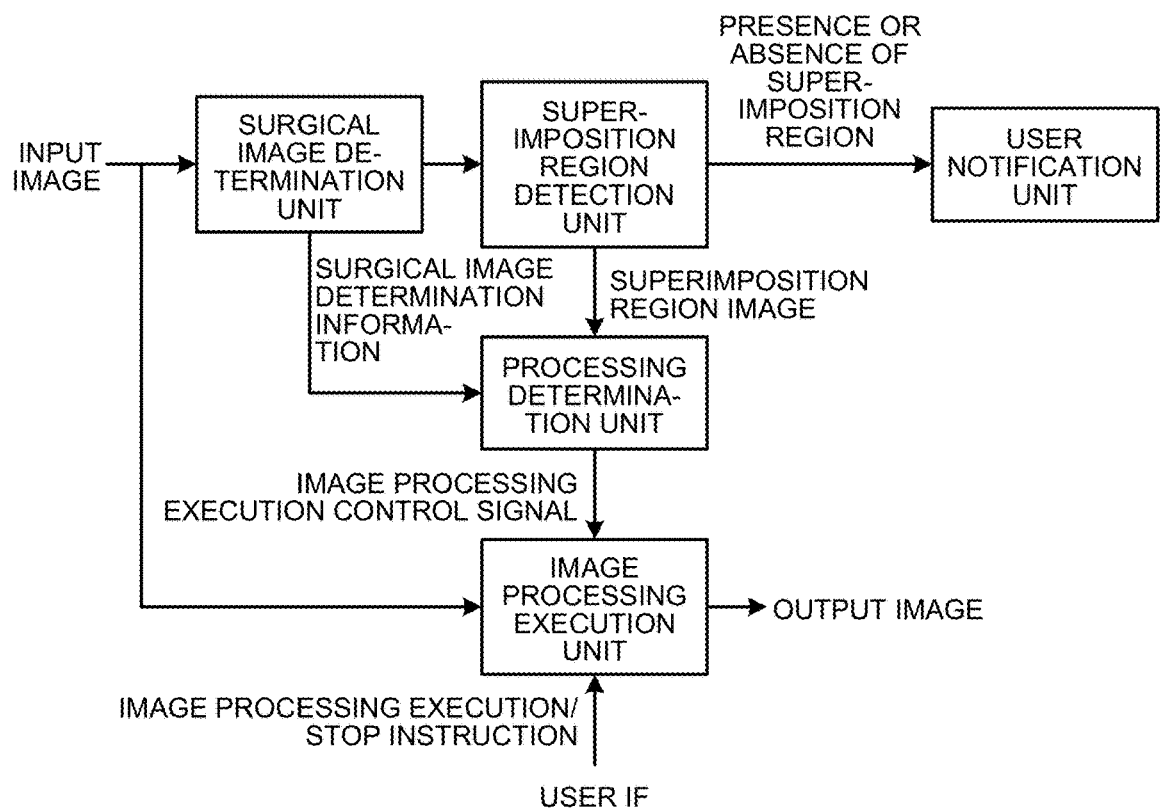
FIG. 9 is a diagram illustrating an example of a conceptual diagram of a functional configuration of a surgical information processing system.

Next, a functional configuration of the surgical information processing apparatus will be described with reference to FIG. 9. FIG. 9 is a diagram illustrating an example of a conceptual diagram of a functional configuration of the surgical information processing system. Specifically, FIG. 9 is a diagram illustrating an example of a functional block diagram of the surgical information processing apparatus.

For example, a surgical image determination unit in FIG. 9 corresponds to the first determination unit 132. In addition, the superimposition region determination unit and the processing determination unit in FIG. 9 correspond to the second determination unit 133. An image processing execution unit in FIG. 9 corresponds to the processing unit 134. A user notification unit in FIG. 9 corresponds to the notification unit 135.

The image processing unit uses, as an input, an output image from the camera control unit 200 illustrated in FIG. 8. The surgical image determination unit determines whether the moving image is a surgical moving image such as images for a surgical endoscopic operation, a robotic operation, a video microscopic operation, or the like. The surgical image determination unit generates information indicating a determination result as to whether the image is a surgical image, and transmits the generated information to the processing determination unit. A superimposition region detection unit detects a region including graphic information or a CT image superimposed by the camera control unit 200. The superimposition region detection unit generates information indicating a superimposition region image. For example, the superimposition region detection unit generates information indicating a position and a range of the superimposition region image. The user notification unit notifies the user of the presence or absence of the superimposition region. The processing determination unit determines the type of processing to be performed based on the information as to whether the moving image is a surgical moving image determined by the surgical image determination unit and based on the presence or absence of the superimposition region detected by the superimposition region detection unit. The processing determination unit determines execution, non-execution, partial execution, or the like regarding image processing in the image processing execution unit, and then generates an image processing control signal instructing specifics of the execution. The image processing execution unit executes image processing such as blur correction, electronic zoom, image rotation processing, PinP processing, and image enhancement. Furthermore, the user can instruct the surgical information processing system to execute or stop the image processing via the user IF.

[1-6-3. Determination of Surgical Image]

Figure 10:
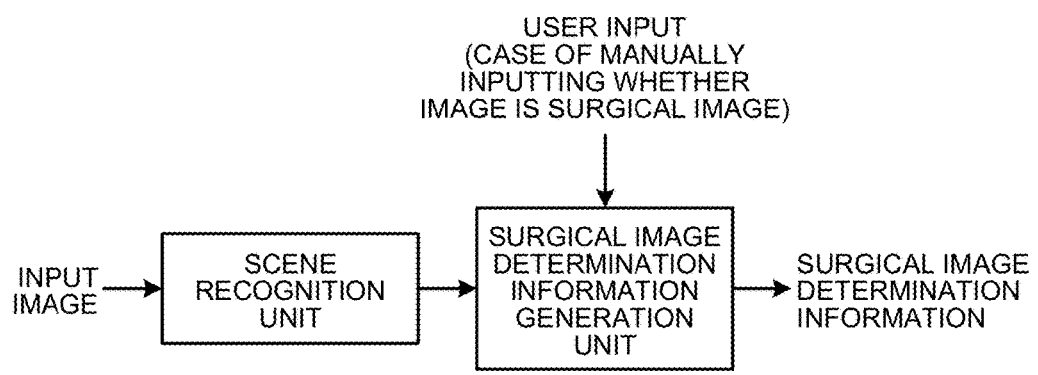
FIG. 10 is a diagram illustrating an example of a conceptual diagram of a functional configuration of a surgical information processing system.

Next, a functional configuration of surgical image determination will be described with reference to FIG. 10. FIG. 10 is a diagram illustrating an example of a conceptual diagram of a functional configuration of the surgical information processing system. Specifically, FIG. 10 is a diagram illustrating an example of a functional block diagram of a surgical image determination unit corresponding to the first determination unit 132.

The surgical information processing apparatus 100 can also input an image other than a surgical moving image (surgical image) such as images for a surgical endoscopic operation, a robotic operation, or a video microscopic operation. The surgical image determination unit (first determination unit 132) includes a scene recognition unit and a surgical image determination information generation unit. For example, the surgical image determination unit recognizes a scene of a surgical image by the scene recognition unit, and then generates determination information indicating whether the image is a surgical image by the surgical image determination information generation unit based on the recognition result. The surgical image determination unit determines whether the input image is a surgical moving image. The surgical image determination unit determines whether a surgical moving image (surgical image) is a surgical image in a case where it is determined that there is a mask, a surgical tool, blood, or the like as a result of recognition using a scene recognition technology such as mask recognition of an endoscope, recognition of surgical tools such as forceps, or blood detection. Note that mask recognition and the like are known techniques, and thus description thereof will be omitted. Furthermore, the surgical information processing apparatus 100 may acquire designation as to whether the image is a surgical moving image by the user. In this case, the user may manually designate whether the image is a surgical moving image.

[1-6-4. Detection of Superimposition Region]

Figure 11:
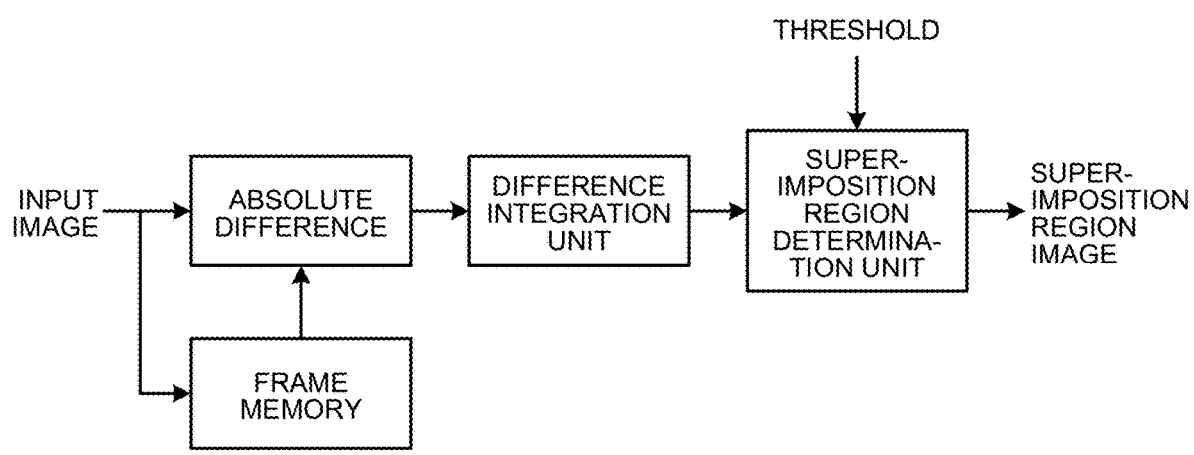
FIG. 11 is a diagram illustrating an example of a conceptual diagram of a functional configuration of a surgical information processing system.
Figure 12:
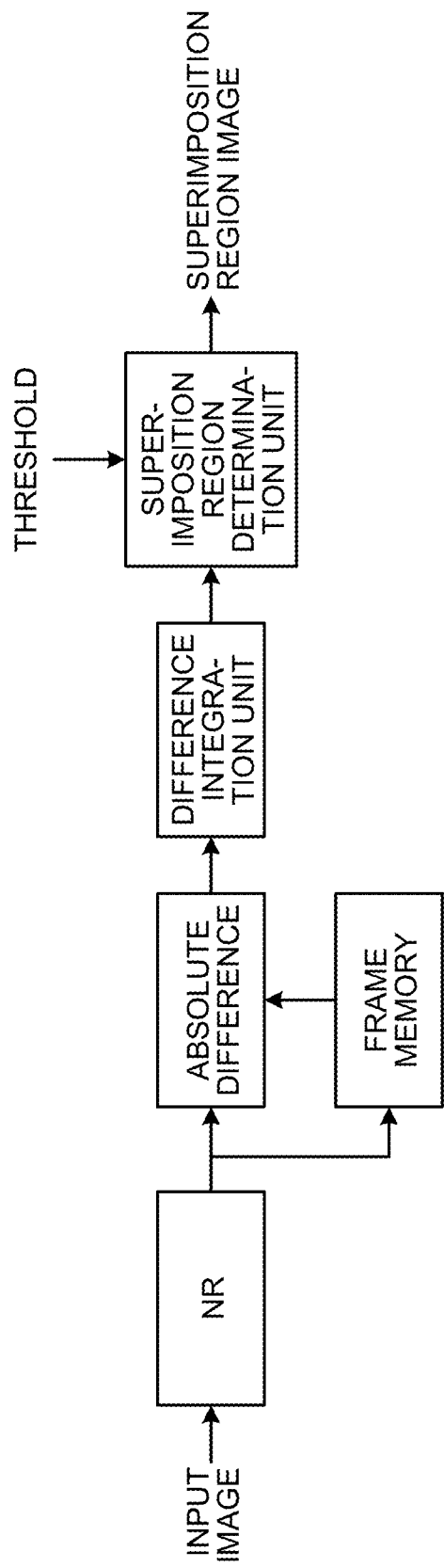
FIG. 12 is a diagram illustrating an example of a conceptual diagram of a functional configuration of a surgical information processing system.
Figure 13:
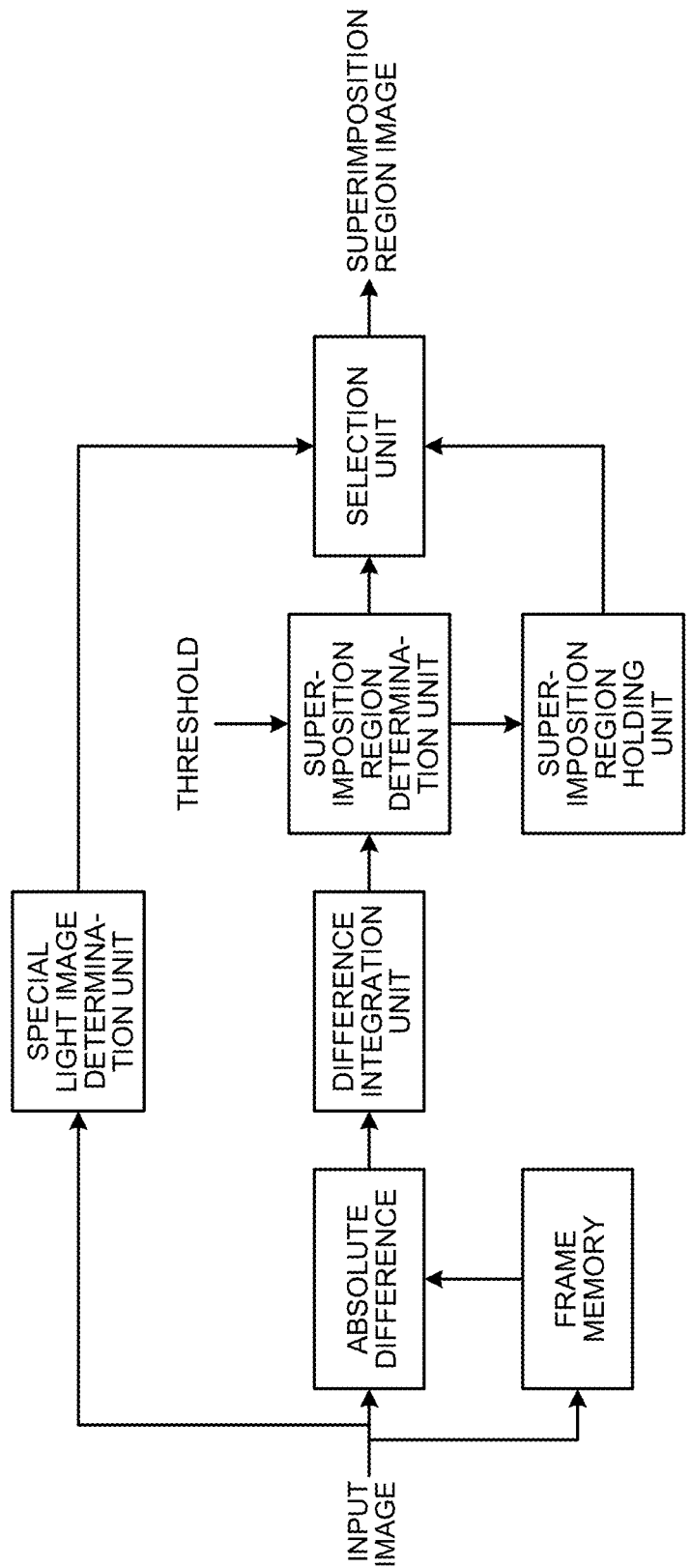
FIG. 13 is a diagram illustrating an example of a conceptual diagram of a functional configuration of a surgical information processing system.

Next, a functional configuration of superimposition region detection will be described with reference to FIGS. 11 to 13. FIGS. 11 to 13 are diagrams illustrating an example of a conceptual diagram of a functional configuration of the surgical information processing system. Specifically, FIGS. 11 to 13 are diagrams illustrating an example of a functional block diagram of a superimposition region detection unit corresponding to the second determination unit 133.

First, a configuration example of FIG. 11 will be described. The superimposition region detection unit (second determination unit 133) includes a difference integration unit and a superimposition region determination unit. The superimposition region detection unit makes a determination by the superimposition region determination unit based on the integration result obtained by the difference integration unit. The superimposition region detection unit holds an image of a preceding frame for the input surgical moving image and calculates a pixel absolute difference between the image of the current frame and the image of the preceding frame to calculate the pixel absolute difference. The superimposition region detection unit integrates the obtained absolute difference in the time direction. The superimposition region detection unit performs threshold processing on the integrated image and detects a region lower than a threshold as a superimposition region.

Next, a configuration example of FIG. 12 will be described. The superimposition region detection unit (second determination unit 133) of FIG. 12 is different from the configuration of FIG. 11 in that it has a noise reduction (NR) function. Surgical scenes include normal light observation scenes observed under a white light source and special light observation scenes such as fluorescence observation. Since the image of the special light observation tends to have a lot of noise, the superimposition region detection unit in FIG. 12 executes NR as preprocessing before the superimposition region determination, and makes the superimposition region determination after noise has been removed.

Next, a configuration example of FIG. 13 will be described. The superimposition region detection unit (second determination unit 133) in FIG. 13 is different from the configuration in FIG. 11 in that it includes a special light image determination unit, a selection unit, and a superimposition region holding unit.

As described above, surgical scenes include normal light observation scenes observed under a white light source and special light observation scenes such as fluorescence observation. In addition, in the special light observation, many regions are lower in level compared to the normal light observation scene and thus have a small absolute difference, leading to occurrence of a case where the regions are erroneously detected as superimposition regions. To handle this, the superimposition region detection unit (second determination unit 133) in FIG. 13 performs the superimposition region detection in the normal light observation scene, and holds the region information in the superimposition region holding unit. The superimposition region detection unit determines whether the input image is the image captured under the normal observation or the image captured under the special light observation by using the special light image determination unit based on the distribution of the image histogram or the like. In the case of the special light observation scene, the superimposition region detection unit selects, as an output, the superimposition region image held in the superimposition region holding unit. In the case of normal observation, the superimposition region detection unit directly outputs the superimposition region image of the superimposition region determination unit.

[1-6-5. User Notification Unit and User IF]

Next, the user notification unit and the user IF will be described. The user notification unit (notification unit 135) notifies the user of the presence or absence of the superimposition region detected by the superimposition region detection unit. The user receives the notification, and in a case where there is the superimposition region, the user can stop the execution of the image processing of the image processing execution unit via the user IF (for example, the input unit or the like). In addition, the user can resume, via the user IF, the execution of the image processing execution unit that has been temporarily stopped.

[1-6-6. Processing Determination Unit]

Figure 14:
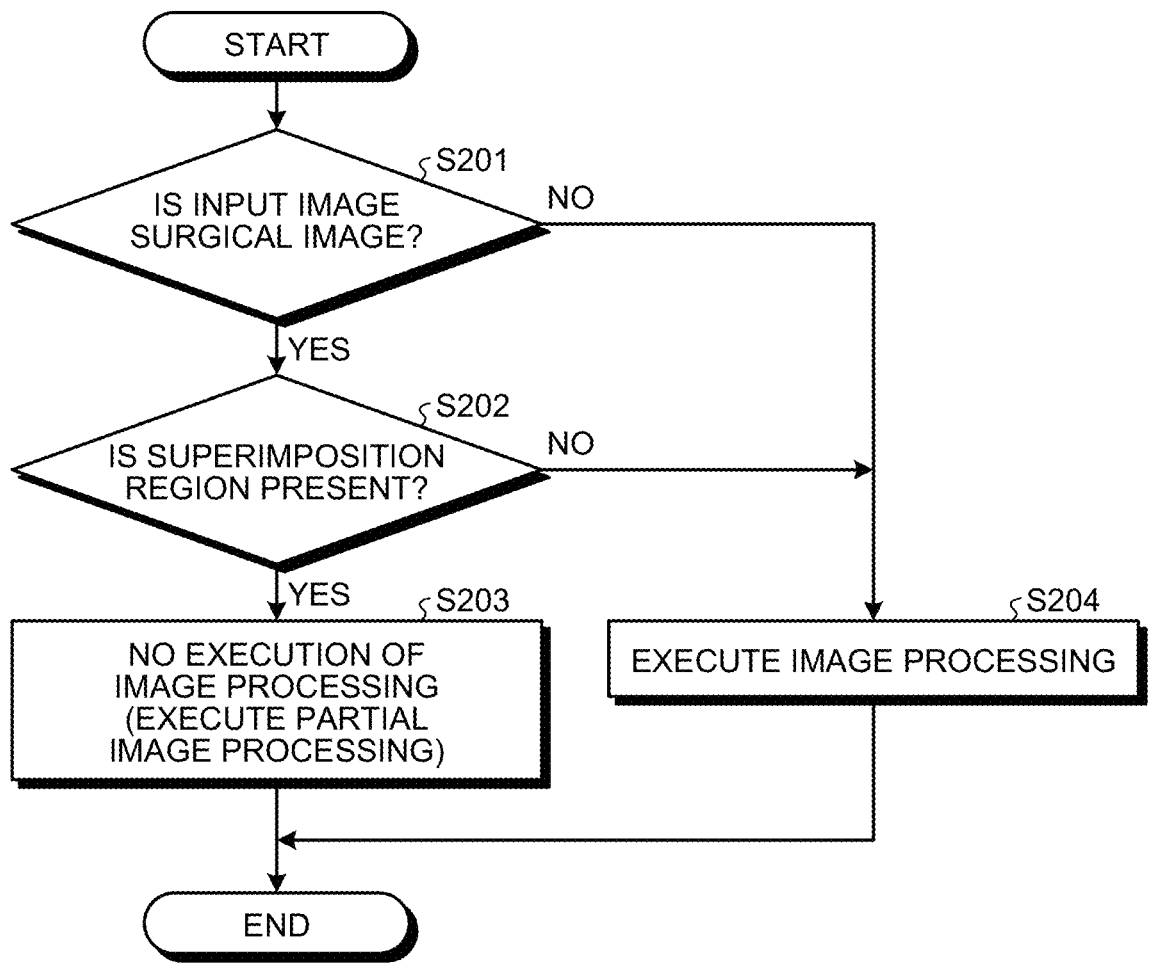
FIG. 14 is a flowchart illustrating an example of a processing procedure by the surgical information processing system.

Next, processing of the processing determination unit will be described with reference to FIG. 14. FIG. 14 is a flowchart illustrating an example of a processing procedure by the surgical information processing system. Specifically, FIG. 14 is a flowchart illustrating an example of a processing procedure by the processing determination unit.

As illustrated in FIG. 14, the surgical information processing apparatus 100 determines whether the input image is a surgical image (step S201). For example, the processing determination unit of the surgical information processing apparatus 100 determines whether the input image is a surgical image based on the information from the surgical image determination unit.

When the input image is a surgical image (step S201: Yes), the surgical information processing apparatus 100 determines whether there is a superimposition region (step S202). For example, when the input image is a surgical image, the processing determination unit of the surgical information processing apparatus 100 determines whether a superimposition region is present in the input image.

When there is a superimposition region (step S202: Yes), the surgical information processing apparatus 100 does not execute image processing or executes partial image processing (step S203). For example, when there is a superimposition region in the input image, the processing determination unit of the surgical information processing apparatus 100 determines to execute the second image processing without executing the first image processing.

In contrast, when the input image is not a surgical image (step S201: No) or when there is no superimposition region (step S202: No), the surgical information processing apparatus 100 executes image processing (step S204). For example, when the input image is not a surgical image or there is no superimposition region in the input image, the processing determination unit of the surgical information processing apparatus 100 determines to execute the first image processing.

As described above, when the surgical image determination unit determines that the input image is an image other than the surgical moving image, the processing determination unit (second determination unit 133) makes a determination to execute image processing by the image processing execution unit. In contrast, when the image is a surgical moving image, the processing determination unit determines whether to or not to execute image processing by the image processing execution unit or to execute partial image processing based on the superimposition region detected by the superimposition region detection unit.

[1-6-7. Image Processing Execution Unit]

When the processing determination unit determines that there is a superimposition region, the image processing execution unit executes various types of image processing control as follows. Note that the following control example is provided as an example, and the image processing execution unit executes various types of control related to image processing. For example, information regarding whether to or not to execute image processing and regarding a region as a target of partial execution is transmitted to the image processing execution unit as an image processing execution control signal. Regarding information including matters as to whether to or not to execute image processing and a region as a target of partial execution, the image processing execution unit receives an image processing execution control signal from the processing determination unit.

The image processing execution unit receives the image processing execution control signal from the processing determination unit, and executes, stops, or partially executes the image processing. Alternatively, the image processing execution unit executes or stops image processing in accordance with an instruction to execute/stop image processing from the user via the user IF. The image processing performed by the image processing execution unit includes blur correction, electronic zoom, image rotation processing, PinP processing, and image enhancement.

For example, the image processing execution unit automatically stops image processing when there is a superimposition region. The image processing execution unit sets a condition for the detected superimposition region, and stops image processing when the condition is satisfied. In this case, the image processing execution unit may set a condition (stop condition) that the area of the superimposition region would be a certain area or more, or that a centroid position of the superimposition region would be in a certain range from the center of the image. The image processing execution unit may stop the image processing based on the stop condition as described above.

[1-7. Processing Mode Examples of Image Processing]

Figure 15:
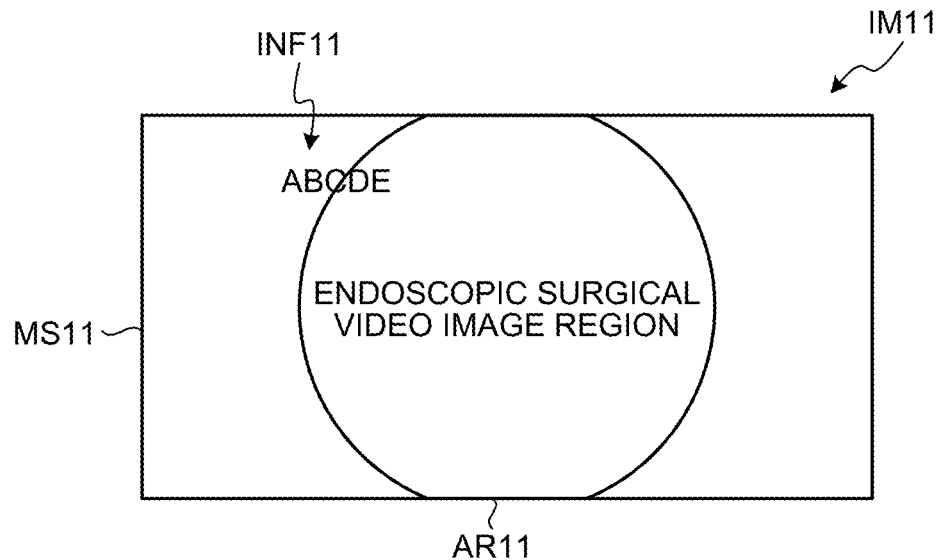
FIG. 15 is a diagram illustrating an example of a processing mode of image processing.
Figure 16:
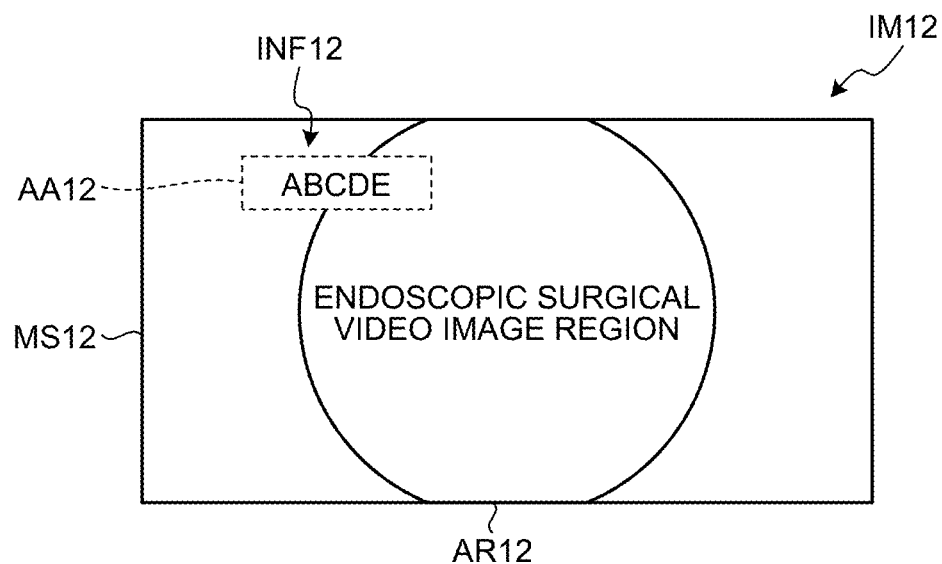
FIG. 16 is a diagram illustrating an example of a processing mode of image processing.
Figure 17:
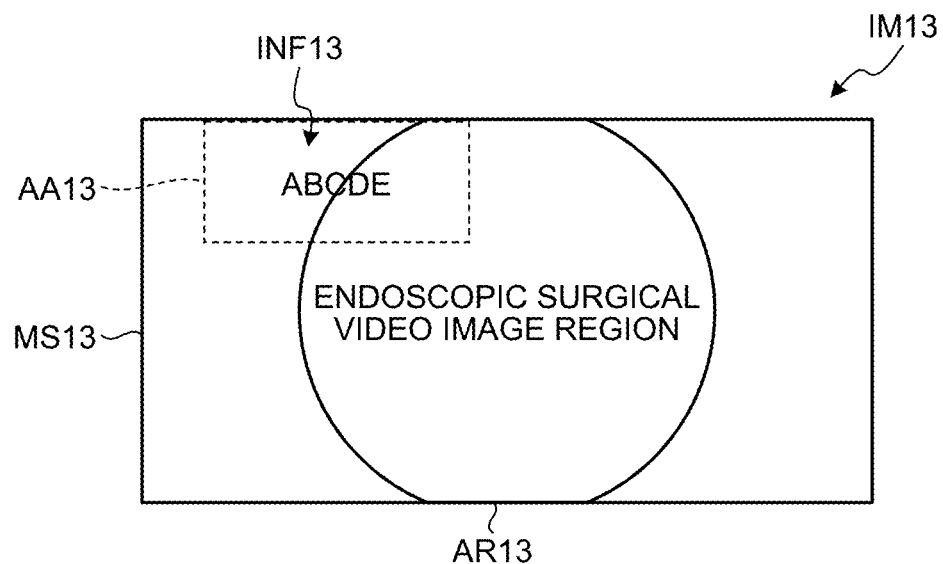
FIG. 17 is a diagram illustrating an example of a processing mode of image processing.
Figure 18:
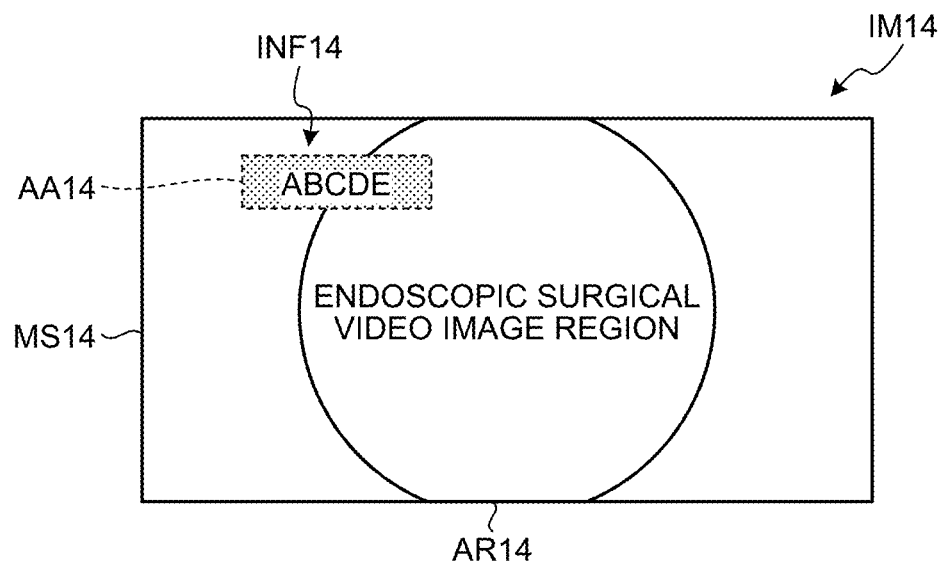
FIG. 18 is a diagram illustrating an example of a processing mode of image processing.

For example, the surgical information processing apparatus 100 stops image processing only within or in the vicinity of the superimposition region, and executes image processing on other regions. In this regard, a processing mode example of image processing will be described with reference to FIGS. 15 to 18. FIGS. 15 to 18 are diagrams illustrating an example of a processing mode of image processing. FIGS. 15 to 18 are diagrams illustrating variations of regions where the image processing is stopped. Specifically, FIG. 15 is a diagram illustrating an example of a first processing mode of image processing. FIG. 16 is a diagram illustrating an example of a second processing mode of the image processing. FIG. 17 is a view illustrating an example of a third processing mode of the image processing. FIG. 18 is a view illustrating an example of a fourth processing mode of the image processing.

[1-7-1. First Processing Mode]

First, the first processing mode will be described with reference to FIG. 15. A surgical image IM11 in FIG. 15 is provided with a mask MS11 and character information INF11. Furthermore, in the example of FIG. 15, the character information INF11 overlaps a region AR11 being an endoscopic surgical video image region. Accordingly, the surgical information processing apparatus 100 stops image processing only in the detected superimposition region. For example, the surgical information processing apparatus 100 stops image processing only in a region where "ABCDE" being the character information INF11 overlaps in the region AR11. The surgical information processing apparatus 100 stops image processing only in a region where "CDE", which is a part of the character information INF11, overlaps in the region AR11.

[1-7-2. Second Processing Mode]

First, the second processing mode will be described with reference to FIG. 16. A surgical image IM12 in FIG. 16 is provided with a mask MS12 and character information INF12. Furthermore, in the example of FIG. 16, the character information INF12 overlaps a region AR12 being an endoscopic surgical video image region. Accordingly, the surgical information processing apparatus 100 stops image processing only in a region AA12 that is a rectangular region surrounding the detected superimposition region. For example, the surgical information processing apparatus 100 stops image processing only in a region where the region AR12 overlaps in the region AR12.

[1-7-3. Third Processing Mode]

First, a third processing mode will be described with reference to FIG. 17. The third processing mode in FIG. 17 is different from the second processing mode in that its rectangular region is larger than that of the second processing mode in FIG. 16. A surgical image IM13 in FIG. 17 is provided with a mask MS13 and character information INF13. Furthermore, in the example of FIG. 17, the character information INF13 overlaps a region AR13 being an endoscopic surgical video image region. Accordingly, the surgical information processing apparatus 100 stops image processing only in a region AA13 that is a rectangular region surrounding the detected superimposition region. For example, the surgical information processing apparatus 100 stops image processing only in a region where the region AR13 overlaps in the region AR13.

[1-7-4. Fourth Processing Mode]

First, a fourth processing mode will be described with reference to FIG. 18. The fourth processing mode in FIG. 18 is different from the first processing mode in FIG. 15 in that processing of portions other than character information in a region AA14 is different from that in the second processing mode. A surgical image IM14 in FIG. 18 is provided with a mask MS13 and character information INF14. Accordingly, the surgical information processing apparatus 100 stops image processing only in the detected superimposition region. For example, the surgical information processing apparatus 100 stops image processing only in a region where "ABCDE" being the character information INF11 overlaps in the region AR14. The surgical information processing apparatus 100 stops image processing only in a region where "CDE", which is a part of the character information INF14, overlaps in the region AR11. In addition, the surgical information processing apparatus 100 performs processing of filling a region other than the superimposition region in the region AA14 with a specific fixed color, or mean or a mode of pixel values of the region.

2. Second Embodiment

[2-1. Configuration of Surgical Information Processing Apparatus According to Second Embodiment of Present Disclosure]

Figure 19:
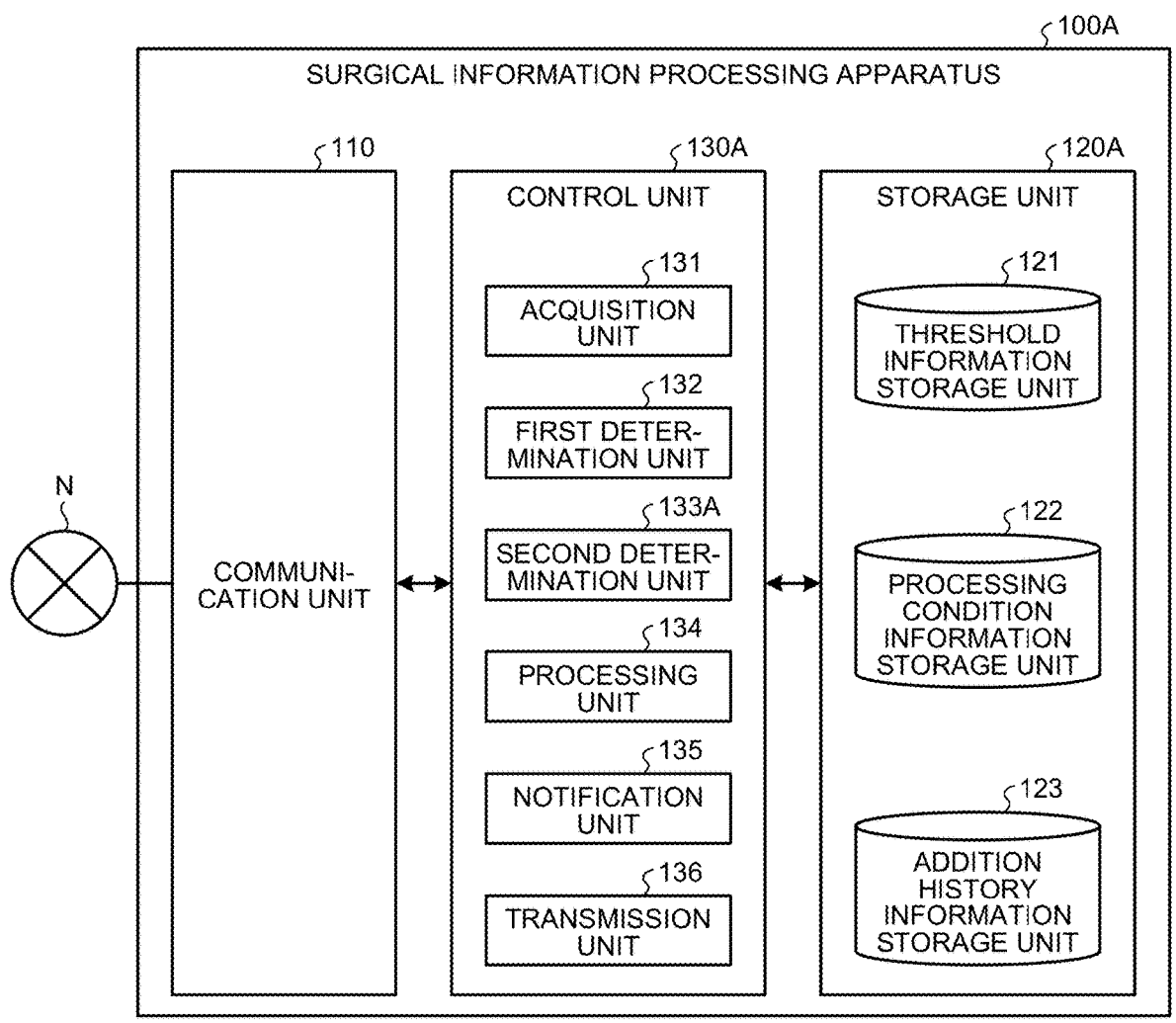
FIG. 19 is a diagram illustrating a configuration example of a surgical information processing apparatus according to a second embodiment of the present disclosure.
Figure 20:
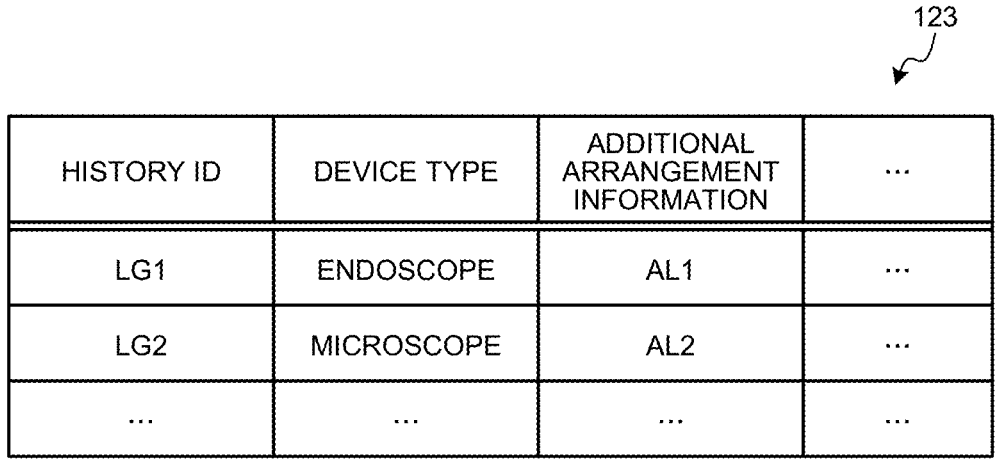
FIG. 20 is a diagram illustrating an example of an addition history information storage unit according to the second embodiment.

The surgical information processing system 1 may execute various types of processing using various types of information, not limited to the processing according to the first embodiment. For example, the surgical information processing system 1 may make a determination using history information. This will be described with reference to FIGS. 19 and 20. FIG. 19 is a diagram illustrating a configuration example of a surgical information processing apparatus according to the second embodiment of the present disclosure. FIG. 20 is a diagram illustrating an example of an addition history information storage unit according to the second embodiment.

Note that description of points similar to those of the first embodiment will be omitted as appropriate. Furthermore, for example, the surgical information processing system 1 according to the second embodiment includes a surgical information processing apparatus 100A instead of the surgical information processing apparatus 100. That is, the surgical information processing system 1 according to the second embodiment includes the medical observation device 10, the image reception device 50, and the surgical information processing apparatus 100A.

First, a configuration of the surgical information processing apparatus according to a second embodiment will be described. As illustrated in FIG. 19, the surgical information processing apparatus 100A includes a communication unit 110, a storage unit 120A, and a control unit 130A.

The storage unit 120A is implemented by a semiconductor memory element such as RAM or flash memory, or a storage device such as a hard disk or an optical disk, for example. As illustrated in FIG. 19, the storage unit 120A according to the second embodiment includes a threshold information storage unit 121, a processing condition information storage unit 122, and an addition history information storage unit 123.

The addition history information storage unit 123 according to the second embodiment stores various types of information related to a history. The addition history information storage unit 123 stores history information regarding arrangement of additional information in the past. FIG. 20 is a diagram illustrating an example of an addition history information storage unit according to the second embodiment. The addition history information storage unit 123 illustrated in FIG. 20 includes items such as "History ID", "Device type", and "Additional arrangement information".

"History ID" indicates identification information for identifying a history. "Device type" indicates a device type corresponding to the history identified by History ID. "Additional arrangement information" indicates information related to arrangement of the additional information identified by History ID.

In the example of FIG. 20, the history identified by History ID "LG1" (namely, History LG1) indicates that the device type is "Endoscope". That is, History LG1 indicates that the arrangement of the additional information in the past related to the endoscope is "AL1". Although the example of FIG. 20 is a case where the additional arrangement information is indicated by an abstract code such as "VL1", the additional arrangement information includes information indicating an arrangement position of the additional information, information indicating a superimposition region, and the like.

Note that the addition history information storage unit 123 may store various types of information according to a purpose, not limited to the above. The addition history information storage unit 123 stores a past history related to the superimposition region.

Returning to FIG. 19, and description will continue. The control unit 130A is implemented by execution of programs stored in the surgical information processing apparatus 100A (for example, an information processing program such as the surgical information processing program according to the present disclosure) by the CPU, MPU, or the like, using RAM or the like as a working area. Furthermore, the control unit 130A is implemented by an integrated circuit such as ASIC or FPGA.

As illustrated in FIG. 19, the control unit 130A includes an acquisition unit 131, a first determination unit 132, a second determination unit 133A, and a transmission unit 136, and actualizes or executes information processing functions and effects described below. The internal configuration of the control unit 130A is not limited to the configuration illustrated in FIG. 19, and may be another configuration as long as it is a configuration that performs information processing described below. Furthermore, the connection relationship of the processing units included in the control unit 130A is not limited to the connection relationship illustrated in FIG. 19, and may be a different connection relationship.

The second determination unit 133A determines whether additional information is attached to a surgical image for a target region that displays additional information corresponding to a device that has captured the surgical image. For example, the second determination unit 133A determines whether additional information is attached to the surgical image based on the information indicating the past superimposition region stored in the addition history information storage unit 123.

[2-2. Conceptual Diagram of Functional Configuration Example of Surgical Information Processing System]

Figure 21:
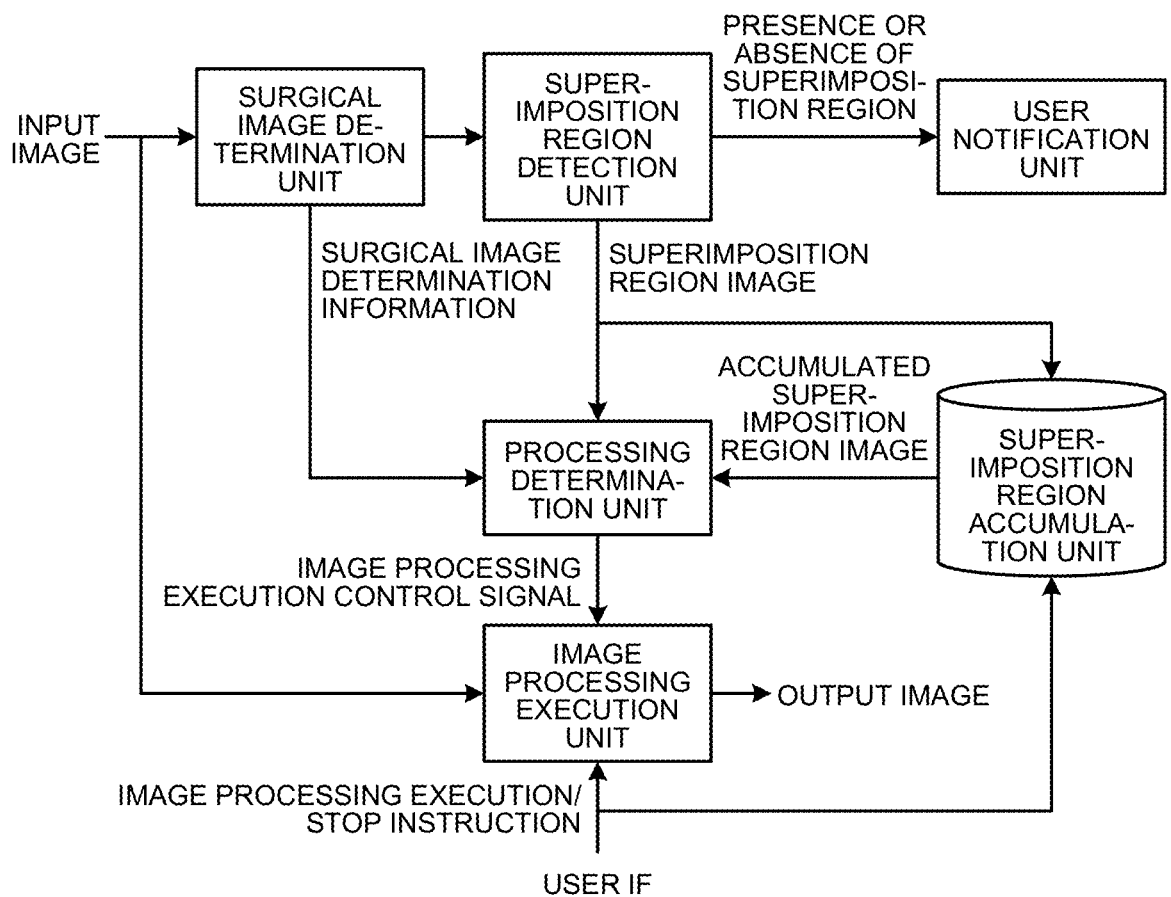
FIG. 21 is a diagram illustrating an example of a conceptual diagram of a functional configuration of a surgical information processing system.

Next, a functional configuration of the surgical information processing apparatus will be described with reference to FIG. 21. FIG. 21 is a diagram illustrating an example of a conceptual diagram of a functional configuration of the surgical information processing system. Specifically, FIG. 21 is a diagram illustrating an example of a functional block diagram of the surgical information processing apparatus. The functional block diagram of the surgical information processing apparatus illustrated in FIG. 21 is different from the functional block diagram of the surgical information processing apparatus illustrated in FIG. 9 in that it includes a superimposition region accumulation unit. Hereinafter, description of the points similar to FIG. 9 will be omitted as appropriate.

For example, the surgical image determination unit in FIG. 21 corresponds to the first determination unit 132. The superimposition region determination unit and the processing determination unit in FIG. 21 correspond to the second determination unit 133A. An image processing execution unit in FIG. 21 corresponds to the processing unit 134. A user notification unit in FIG. 21 corresponds to the notification unit 135. An image processing execution unit in FIG. 21 corresponds to the processing unit 134. The superimposition region accumulation unit in FIG. 21 corresponds to the addition history information storage unit 123.

With the surgical information processing apparatus 100A, the superimposition region detection unit (second determination unit 133A) notifies a user of the presence or absence of the superimposition region by using the user notification unit, and thereafter, the user can instruct execution/stop of the image processing via the user IF. The surgical information processing apparatus 100A stores, in the superimposition region accumulation unit, a superimposition region for a case where the superimposition region detection unit detected that there is a superimposition region and the user stopped image processing, as a history. Thereafter, the processing determination unit (second determination unit 133A) compares the current superimposition region image detected by the superimposition region detection unit with the superimposition image accumulated in the superimposition region accumulation unit, and determines to stop or partially stop the image processing in a case where the current superimposition region image and the accumulated superimposition region image are the same region. In contrast, in a case where the superimposition region image and the accumulated superimposition region image are different regions, the processing determination unit determines to execute image processing.

As described above, the surgical information processing apparatus 100A refers to the history of the superimposition region where the user manually has stopped in the past with respect to the image on which the graphics such as the OSD and the GUI, the CT image, and the like are superimposed, and stops image processing only with the superimposition region where the user has manually stopped in the past. This makes it possible to stop the image processing only with the superimposition region where the user has felt uncomfortable in the past, leading to the reduction of the discomfort in the user.

3. Other Embodiments

It is also allowable to execute various processes, not limited to the processes according to the first embodiment and the second embodiment. This point will be described below. Although the following is an exemplary a case where the surgical information processing apparatus 100 performs processing, the surgical information processing apparatus 100A may perform the processing.

3-1. Determination Example Based on Luminance

For example, the surgical information processing apparatus 100 may make a determination using luminance information. In this case, the surgical information processing apparatus 100 may make the determination using two thresholds. For example, the surgical information processing apparatus 100 may make the determination using a threshold for difference (also referred to as a "first threshold") and a threshold for luminance (also referred to as a "second threshold"). The surgical information processing apparatus 100 may make a determination on additional information based on a comparison between the first threshold and the summed value of the absolute difference of the plurality of surgical images and based on a comparison between the second threshold and the summed value of the luminance values of the plurality of surgical images.

Figures 22, 23:
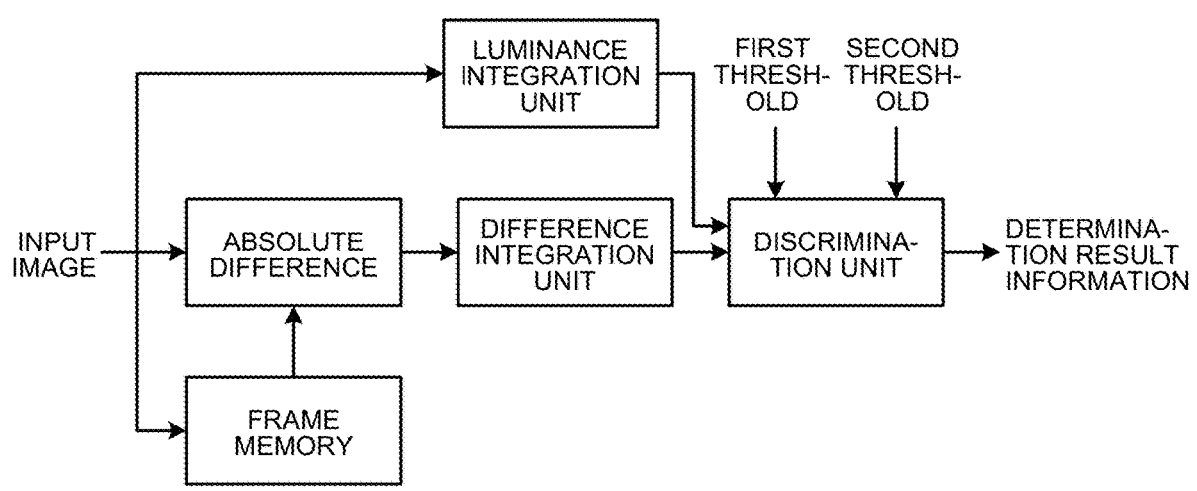
FIG. 22 is a diagram illustrating an example of a threshold information storage unit according to a modification of the present disclosure.
FIG. 23 is a diagram illustrating an example of a conceptual diagram of a functional configuration of a surgical information processing system.

In this case, the surgical information processing apparatus 100 uses threshold information as illustrated in a threshold information storage unit 121A in FIG. 22. The surgical information processing apparatus 100 according to a modification includes the threshold information storage unit 121A in FIG. 22 in the storage unit 120 instead of the threshold information storage unit 121 in FIG. 4.

The threshold information storage unit 121A according to the modification stores various types of information related to thresholds. The threshold information storage unit 121A stores various types of information related to thresholds used for various determinations. FIG. 22 is a diagram illustrating an example of a threshold information storage unit according to a modification of the present disclosure. The threshold information storage unit 121A illustrated in FIG. 22 includes items such as "Threshold ID", "Target", and "Threshold".

"Threshold ID" indicates identification information for identifying the threshold. "Target" indicates a target to which the threshold is applied. "Threshold" indicates a specific value of the threshold identified by the corresponding threshold ID.

In the example of FIG. 22, the threshold identified by Threshold ID "TH1" (namely, Threshold TH1) indicates the first threshold whose target is "Absolute difference". That is, the threshold TH1 indicates that the threshold TH1 is used for comparison with the absolute difference. In this case, the threshold TH1 indicates a value used for comparison with the absolute difference, and a value used for determination of the presence or absence of additional information. The value of the threshold TH1 indicates "VL1". In the example of FIG. 22, the threshold TH1 is indicated by an abstract code such as "VL1", but the value of the threshold TH1 is a specific numerical value in practice.

The threshold identified by Threshold ID "TH2" (namely, Threshold TH2) indicates a second threshold whose target is "luminance". That is, the threshold TH2 indicates that the threshold TH2 is used for comparison with the absolute difference. In this case, the threshold TH2 indicates a value used for comparison with the absolute difference, and a value used for determination of the presence or absence of the additional information. The value of the threshold TH2 indicates "VL2". In the example of FIG. 22, the threshold TH2 is indicated by an abstract code such as "VL2", but the value of the threshold TH2 is a specific numerical value in practice.

Note that the threshold information storage unit 121A is not limited to the above, and may store various types of information depending on the purpose.

The surgical information processing apparatus 100 discriminates a mask image and on-screen display (OSD) information by using information stored in the threshold information storage unit 121A. The surgical information processing apparatus 100 discriminates between a mask image and on-screen display (OSD) information based on a comparison between a first threshold and a summed value of the absolute differences of a plurality of surgical images and a comparison between a second threshold and a summed value of the luminance values of the plurality of surgical images.

[3-1-1. Conceptual Diagram of Functional Configuration Example of Surgical Information Processing System]

Next, a functional configuration of the surgical information processing apparatus will be described with reference to FIG. 23. FIG. 23 is a diagram illustrating an example of a conceptual diagram of a functional configuration of the surgical information processing system. Specifically, FIG. 23 is a diagram illustrating an example of a functional block diagram of a superimposition region detection unit corresponding to the second determination unit 133. The functional block diagram of the surgical information processing apparatus illustrated in FIG. 23 is different from the functional block diagram of the surgical information processing apparatus illustrated in FIG. 11 in that the luminance integrated value and the two thresholds are used and that a discrimination unit is provided. Hereinafter, description of the points similar to FIG. 11 will be omitted as appropriate.

The superimposition region detection unit (second determination unit 133) includes a luminance integrated value, a difference integration unit, and a discrimination unit. The superimposition region detection unit performs discrimination by the discrimination unit based on the integration result obtained by the difference integration unit and the integration result by the luminance integrated values. The discrimination unit generates information indicating a determination result. The superimposition region detection unit makes a determination by the discrimination unit based on the integration result obtained by the difference integration unit. The superimposition region detection unit holds an image of a preceding frame for the input surgical moving image and calculates a pixel absolute difference between the image of the current frame and the image of the preceding frame to calculate the pixel absolute difference. The superimposition region detection unit integrates the absolute difference in the time direction to calculate an integrated value of difference. The superimposition region detection unit integrates the luminance value of each image in the time direction for the input surgical moving image to calculate a luminance integrated value. The superimposition region detection unit performs threshold processing on the integrated image.

For example, the superimposition region detection unit discriminates a region where the integrated value of difference is lower than the first threshold and the luminance integrated value is lower than the second threshold as a mask. For example, the superimposition region detection unit discriminates a region where the integrated value of difference is lower than the first threshold and the luminance integrated value is the second threshold or more as OSD information. The discrimination unit generates information indicating a determination result as to whether the information is a mask or OSD information.

[3-1-2. Example of Determination Based on Luminance]

Figure 24:
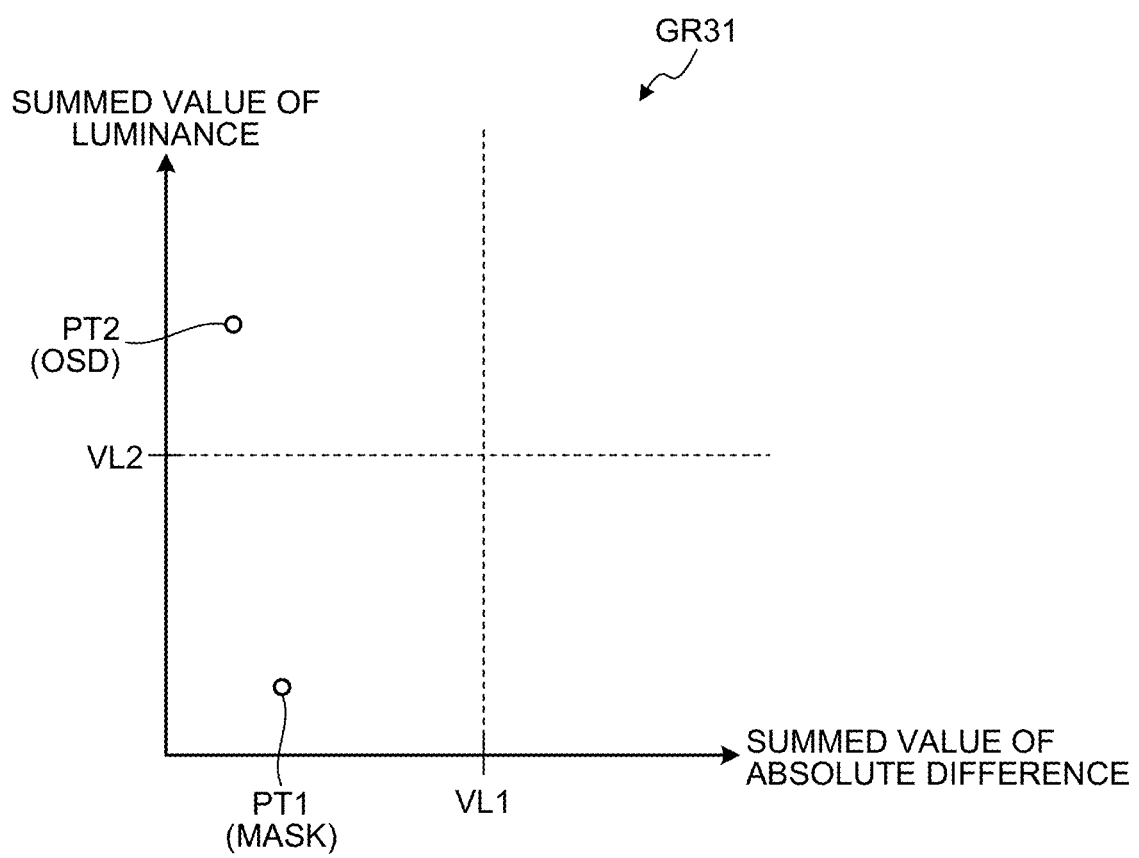
FIG. 24 is a diagram illustrating an example of discrimination between a mask and an OSD.

The above-described discrimination example will be described with reference to FIG. 24. FIG. 24 is a diagram illustrating an example of discrimination between a mask and an OSD. Graph GR31 in FIG. 24 illustrates a graph having a summed value of luminance (integrated value of luminance) on the vertical axis and having a summed valued of absolute differences (integrated value of differences) on the horizontal axis. In this manner, the surgical information processing apparatus 100 makes a determination on the additional information by defining the summed value of the absolute differences of the plurality of surgical images as the first axis and the summed value of the luminance values of the plurality of surgical images as the second axis. The surgical information processing apparatus 100 discriminates between a mask and OSD information by using an integrated value of difference integrated in a time direction for each pixel and an integrated value for luminance integrated in the time direction for each pixel.

In the example of FIG. 24, the surgical information processing apparatus 100 determines a pixel PT1 plotted in a region smaller than the first threshold "VL1" in the horizontal axis direction and smaller than the second threshold "VL2" in the vertical axis direction, as a mask. In addition, the surgical information processing apparatus 100 determines a pixel PT2 plotted in a region smaller than the first threshold "VL1" in the horizontal axis direction and the second threshold "VL2" or more in the vertical axis direction, as OSD information. The surgical information processing apparatus 100 discriminates between a mask and OSD information by using information regarding an absolute difference in a time direction and information regarding a luminance value (luminance) for each pixel. In this case, the surgical information processing apparatus 100 discriminates between the mask and the OSD information by using the first threshold for the absolute difference and the second threshold for the luminance. In this manner, the surgical information processing apparatus 100 can appropriately determine the additional information by discriminating between the mask and the OSD information using two thresholds.

With the above-described processing, the surgical information processing apparatus 100 can appropriately discriminate additional information such as OSD information. Furthermore, the surgical information processing apparatus 100 may determine a pixel having an integrated value for difference being the first threshold "VL1" or more as a pixel corresponding to a surgical image. For example, in the example of FIG. 24, the surgical information processing apparatus 100 may determine that pixel plotted in a region being the first threshold "VL1" or more in the horizontal axis direction is a pixel corresponding to a surgical image. Note that, in a case where the surgical information processing apparatus 100 does not discriminate between the mask and the additional information such as OSD information, as described above, the mask may also be determined as additional information. For example, the surgical information processing apparatus 100 may determine whether additional information including a mask is attached.

3-2. Other Configuration Examples

The processes according to the above-described embodiments and modifications may be performed in various different forms (modifications) other than the above-described embodiments and modifications. For example, an apparatus that performs image processing (the surgical information processing apparatus 100 or the surgical information processing apparatus 100A) may be integrated with a device that displays an image. Note that the above is an example, and the surgical information processing system 1 may be implemented by various configurations.

3-3. Others

Furthermore, among each process described in the above embodiments, all or a part of the processes described as being performed automatically can be manually performed, or the processes described as being performed manually can be performed automatically by a known method. In addition, the processing procedures, specific names, and information including various data and parameters illustrated in the above specifications or drawings can be changed in any manner unless otherwise specified. For example, various types of information illustrated in each of the drawings are not limited to the information illustrated.

In addition, each of the components of each of the illustrated devices is provided as a functional and conceptional illustration and thus does not necessarily have to be physically configured as illustrated. That is, the specific form of distribution/integration of each of devices is not limited to those illustrated in the drawings, and all or a part thereof may be functionally or physically distributed or integrated into arbitrary units according to various loads and use conditions.

Furthermore, the above-described embodiments and modifications can be appropriately combined within a range implementable without contradiction of processes.

The effects described in the present specification are merely examples, and thus, there may be other effects, not limited to the exemplified effects.

4. Effects According to Present Disclosure

As described above, the surgical information processing apparatus (the surgical information processing apparatuses 100 and 100A in the embodiments) according to the present disclosure includes the acquisition unit (the acquisition unit 131 in the embodiments), the determination unit (the second determination units 133 and 133A in the embodiments), and the processing unit (the processing unit 134 in the embodiments). The acquisition unit acquires a surgical image. The determination unit determines whether additional information is attached to the surgical image acquired by the acquisition unit. The processing unit performs the first image processing when the determination unit has determined that additional information is not attached, and does not perform the first image processing when it is determined that additional information is attached.

With this configuration, the surgical information processing apparatus according to the present disclosure determines whether additional information is attached to the surgical image, performs the first image processing in a case where it is determined that additional information is not attached, and performs the first image processing in a case where it is determined that additional information is attached, making it possible to appropriately perform image processing according to the surgical image.

In addition, the acquisition unit acquires a surgical image from a medical observation device. This enables the surgical information processing apparatus to appropriately perform image processing on the surgical image acquired from the medical observation device.

Furthermore, in a case where it is determined that the additional information is attached, the processing unit performs second image processing different from the first image processing. With this configuration, by performing the first image processing on the image to which additional information is not attached and performing the second image processing on the image to which additional information is attached, the surgical information processing apparatus can appropriately perform image processing according to the surgical image.

Furthermore, the first image processing is image processing targeted for an entire portion of the surgical image. The second image processing includes image processing of a type same as the type of the first image processing, the processing being targeted for a region of the surgical image other than the additional information region corresponding to the additional information. With this configuration, by performing, on the image to which additional information is attached, the image processing of the type same as the type of the first image processing, the processing being targeted for a region other than the additional information region corresponding to the additional information, the surgical information processing apparatus can appropriately perform image processing according to the surgical image.

Furthermore, the second image processing includes image processing different from the first image processing, the processing being targeted for the additional information region. With this configuration, by performing, on the image to which additional information is attached, the image processing of the type different from the type of the first image processing, the image processing being targeted for the additional information region, the surgical information processing apparatus can appropriately perform image processing according to the surgical image.

The acquisition unit acquires metadata of a surgical image. The determination unit determines whether additional information is attached to the surgical image based on the metadata acquired by the acquisition unit. With this configuration, the surgical information processing apparatus can appropriately determine whether additional information is attached to the surgical image based on the metadata of the surgical image, making it possible to appropriately perform image processing according to the surgical image.

Furthermore, the determination unit determines whether additional information is attached to the surgical image based on a result of the image analysis on the surgical image. With this configuration, the surgical information processing apparatus can appropriately determine whether additional information is attached to the surgical image based on the image analysis on the surgical image, making it possible to appropriately perform image processing according to the surgical image.

Furthermore, the acquisition unit acquires user setting information indicating setting made by the user. The determination unit determines whether additional information is attached to the surgical image based on the user setting information acquired by the acquisition unit. With this configuration, the surgical information processing apparatus can appropriately determine whether additional information is attached to the surgical image based on the user setting information indicating the setting made by the user, making it possible to appropriately perform image processing according to the surgical image.

Furthermore, the acquisition unit acquires connected device information indicating a device connected to the surgical information processing apparatus. The determination unit determines whether additional information is attached to the surgical image based on the connected device information acquired by the acquisition unit. With this configuration, the surgical information processing apparatus can appropriately determine whether additional information is attached to the surgical image based on the connected device information indicating the device connected to the surgical information processing apparatus, making it possible to appropriately perform image processing according to the surgical image.

The determination unit makes a determination on a region of the additional information attached to the surgical image. This enables the surgical information processing apparatus to determine the region of the additional information attached to the surgical image, making it possible to appropriately perform image processing according to the determined region.

Furthermore, the determination unit makes a determination on a region of additional information that is character information attached to the surgical image. This enables the surgical information processing apparatus to determine the region of the additional information being character information attached to the surgical image, making it possible to appropriately perform image processing according to the determined region.

Furthermore, the first image processing includes at least one of zoom, camera shake correction, rotation correction, or picture in picture (PinP). With this configuration, by performing image processing including at least one of zoom, camera shake correction, rotation correction, or PinP on the image to which additional information is not attached, the surgical information processing apparatus can appropriately perform image processing according to the surgical image.

Furthermore, the acquisition unit acquires a plurality of surgical images including the surgical image. The determination unit determines whether additional information is attached to the surgical image by comparing the plurality of surgical images. With this configuration, by comparing the plurality of surgical images, the surgical information processing apparatus can appropriately determine whether additional information is attached to the surgical image. Therefore, the surgical information processing apparatus can appropriately perform image processing according to the surgical image based on the determination result.

Furthermore, the determination unit determines a portion in which the difference between the pixel values of the plurality of surgical images does not exceed a threshold as additional information. With this configuration, the surgical information processing apparatus can determine a portion in which the difference between the pixel values of the plurality of surgical images does not exceed the threshold as additional information. Therefore, the surgical information processing apparatus can appropriately perform image processing according to the surgical image based on the determination result.

In addition, the determination unit makes a determination by changing the threshold according to the device that has captured the surgical image. With this configuration, by performing determination while changing the threshold according to the device that has captured the surgical image, the surgical information processing apparatus can appropriately determine whether additional information is attached. Therefore, the surgical information processing apparatus can appropriately perform image processing according to the surgical image based on the determination result.

Furthermore, the acquisition unit acquires information indicating a target region that displays additional information corresponding to a device that has captured a surgical image. The determination unit determines whether additional information is attached to the surgical image for the target region. With this configuration, by determining whether additional information is attached to the surgical image for the target region that displays the additional information corresponding to the device that has captured the surgical image, the surgical information processing apparatus can appropriately determine whether additional information is attached to the surgical image. Therefore, the surgical information processing apparatus can appropriately perform image processing according to the surgical image based on the determination result.

Furthermore, when a plurality of surgical images including a special light image and an observation light image are acquired, the determination unit determines whether additional information is attached by making a comparison using the observation light image. With this configuration, by determining whether additional information is attached using an observation light image, out of the special light image and the observation light image, the surgical information processing apparatus can appropriately determine whether additional information is attached to the surgical image. Therefore, the surgical information processing apparatus can appropriately perform image processing according to the surgical image based on the determination result.

The acquisition unit also acquires a first threshold that is a threshold for difference and a second threshold that is a threshold for luminance. The determination unit determines the additional information based on comparison between the first threshold and the summed value of the absolute differences of the plurality of surgical images and comparison between the second threshold and the summed value of the luminance values of the plurality of surgical images. With this configuration, by determining additional information using the first threshold that is the threshold for the difference and the second threshold that is the threshold for the luminance, the surgical information processing apparatus can appropriately determine the additional information attached to the surgical image. Therefore, the surgical information processing apparatus can appropriately perform image processing according to the surgical image based on the determination result.

5. Hardware Configuration

Figure 25:
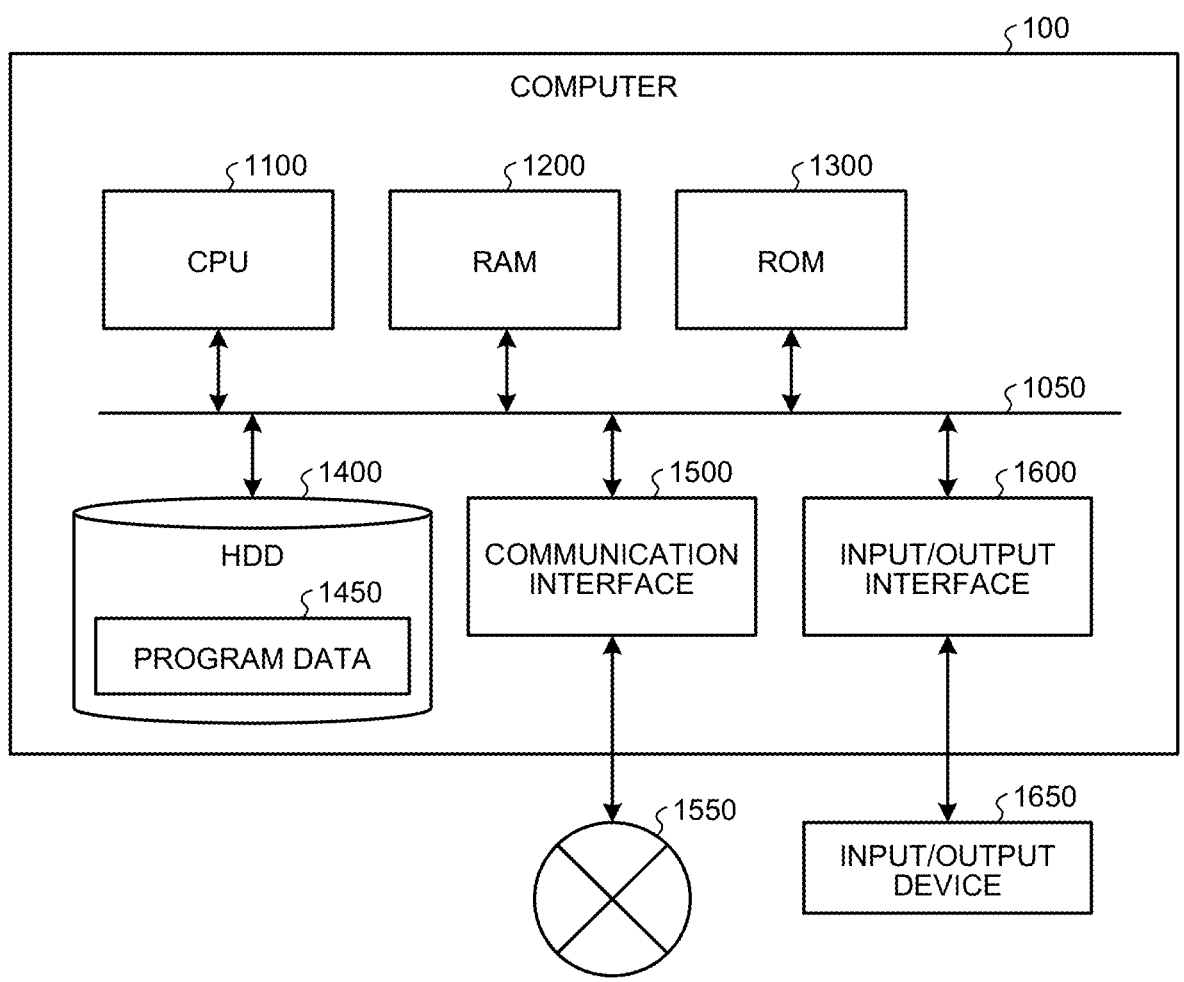
FIG. 25 is a hardware configuration diagram illustrating an example of a computer that implements functions of a surgical information processing apparatus.

The information apparatus such as the surgical information processing apparatuses 100 and 100A according to the above-described embodiments and modifications are implemented by a computer 1000 having a configuration as illustrated in FIG. 25, for example. FIG. 25 is a hardware configuration diagram illustrating an example of the computer 1000 that implements the functions of an information processing apparatus (computer) such as the surgical information processing apparatuses 100 and 100A. Hereinafter, the surgical information processing apparatus 100 according to the embodiment will be described as an example. The computer 1000 includes a CPU 1100, RAM 1200, read only memory (ROM) 1300, a hard disk drive (HDD) 1400, a communication interface 1500, and an input/output interface 1600. Individual components of the computer 1000 are interconnected by a bus 1050.

The CPU 1100 operates based on a program stored in the ROM 1300 or the HDD 1400 so as to control each of components. For example, the CPU 1100 develops the program stored in the ROM 1300 or the HDD 1400 into the RAM 1200 and executes processes corresponding to various programs.

The ROM 1300 stores a boot program such as a basic input output system (BIOS) executed by the CPU 1100 when the computer 1000 starts up, a program dependent on hardware of the computer 1000, or the like.

The HDD 1400 is a non-transitory computer-readable recording medium that records a program executed by the CPU 1100, data used by the program, or the like. Specifically, the HDD 1400 is a recording medium that records an information processing program (surgical information processing program, and the like) according to the present disclosure, which is an example of program data 1450.

The communication interface 1500 is an interface for connecting the computer 1000 to an external network 1550 (for example, the Internet). For example, the CPU 1100 receives data from other devices or transmits data generated by the CPU 1100 to other devices via the communication interface 1500.

The input/output interface 1600 is an interface for connecting between an input/output device 1650 and the computer 1000. For example, the CPU 1100 receives data from an input device such as a keyboard or a mouse via the input/output interface 1600. In addition, the CPU 1100 transmits data to an output device such as a display, a speaker, or a printer via the input/output interface 1600. Furthermore, the input/output interface 1600 may function as a media interface for reading a program or the like recorded on predetermined recording medium (or simply medium). Examples of the media include optical recording media such as a digital versatile disc (DVD) or a phase change rewritable disk (PD), a magneto-optical recording medium such as a magneto-optical disk (MO), a tape medium, a magnetic recording medium, or semiconductor memory.

For example, when the computer 1000 functions as the surgical information processing apparatus 100 according to the embodiment, the CPU 1100 of the computer 1000 executes the information processing program loaded on the RAM 1200 so as to implement the functions of the control unit 130 and the like. Furthermore, the HDD 1400 stores the information processing program according to the present disclosure or data in the storage unit 120. While the CPU 1100 executes program data 1450 read from the HDD 1400, the CPU 1100 may acquire these programs from another device via the external network 1550, as another example.

Note that the present technology can also have the following configurations.

(1)

A surgical information processing apparatus comprising:
an acquisition unit that acquires a surgical image;
a determination unit that determines whether additional information is attached to the surgical image acquired by the acquisition unit; and
a processing unit that performs first image processing when the determination unit has determined that the additional information is not attached, and does not perform the first image processing when the determination unit has determined that the additional information is attached.

(2)

The surgical information processing apparatus according to (1),
wherein the acquisition unit
acquires the surgical image from a medical observation device.

(3)

The surgical information processing apparatus according to (1) or (2),
wherein, in a case where it is determined that the additional information is attached, the processing unit
performs second image processing different from the first image processing.

(4)

The surgical information processing apparatus according to (3),
wherein the first image processing is
image processing targeted for an entire portion of the surgical image, and
the second image processing includes
image processing of a same type as the first image processing, the image processing being targeted for a region in the surgical image other than an additional information region corresponding to the additional information.

(5)

The surgical information processing apparatus according to (4),
wherein the second image processing includes
image processing of a type different from the type of the first image processing, the image processing being targeted for the additional information region.

(6)

The surgical information processing apparatus according to (4) or (5),
in which the second image processing includes
pixel filling processing targeted for the additional information region.

(7)

The surgical information processing apparatus according to any one of (1) to (6),
wherein the acquisition unit
acquires metadata of the surgical image, and
the determination unit
determines whether the additional information is attached to the surgical image based on the metadata acquired by the acquisition unit.

(8)

The surgical information processing apparatus according to (7),
in which the acquisition unit
acquires the metadata including information regarding digital imaging and communications in medicine (DICOM) of the surgical image.

(9)

The surgical information processing apparatus according to any one of (1) to (8),
wherein the determination unit
determines whether the additional information is attached to the surgical image based on a result of image analysis on the surgical image.

(10)

The surgical information processing apparatus according to (9),
in which the determination unit
determines whether the additional information is attached to the surgical image based on a result of the image analysis regarding a color of the surgical image.

(11)

The surgical information processing apparatus according to (9) or (10),
in which the determination unit
determines whether the additional information is attached to the surgical image based on a result of the image analysis of the surgical image using machine learning.

(12)

The surgical information processing apparatus according to any one of (1) to (11),
wherein the acquisition unit
acquires user setting information indicating settings made by a user, and
the determination unit
determines whether the additional information is attached to the surgical image based on the user setting information acquired by the acquisition unit.

(13)

The surgical information processing apparatus according to any one of (1) to (12),
wherein the acquisition unit
acquires connected device information indicating a device connected to the surgical information processing apparatus, and
the determination unit
determines whether the additional information is attached to the surgical image based on the connected device information acquired by the acquisition unit.

(14)

The surgical information processing apparatus according to any one of (1) to (13),
wherein the determination unit
determines a region of the additional information attached to the surgical image.

(15)

The surgical information processing apparatus according to (14),
in which the determination unit
determines a region of the additional information attached to the surgical image corresponding to zoom processing.

(16)

The surgical information processing apparatus according to (14) or (15),
in which the determination unit
determines a region of the additional information that is a frozen image to be attached to the surgical image.

(17)

The surgical information processing apparatus according to any one of (14) to (16), wherein the determination unit
determines a region of the additional information being character information attached to the surgical image.

(18)
The surgical information processing apparatus according to any one of (14) to (17),
in which the determination unit
determines a region of the additional information that is a frame to be attached to the surgical image.

(19)
The surgical information processing apparatus according to any one of (14) to (18),
in which the determination unit
determines a region of the additional information, the additional information having transparency and attached to the surgical image.

(20)
The surgical information processing apparatus according to any one of (1) to (19),
wherein the first image processing includes
at least one of zoom, camera shake correction, rotation correction, or Picture in Picture (PinP).

(21)
The surgical information processing apparatus according to any one of (1) to (20),
wherein the acquisition unit
acquires a plurality of surgical images including the surgical image, and
the determination unit
determines whether additional information is attached to the surgical image by comparing the plurality of surgical images.

(22)
The surgical information processing apparatus according to (21),
in which the determination unit
determines whether additional information is attached to the surgical image based on comparison of colors of the plurality of surgical images.

(23)
The surgical information processing apparatus according to (21) or (22),
wherein the determination unit
determines a portion in which a difference between pixel values of the plurality of surgical images does not exceed a threshold as additional information.

(24)
The surgical information processing apparatus according to (23),
wherein the determination unit
makes a determination by changing the threshold according to a device that has captured the surgical image.

(25)
The surgical information processing apparatus according to any one of (21) to (24),
wherein the acquisition unit
acquires information indicating a target region that displays the additional information corresponding to a device that has captured the surgical image, and
the determination unit
determines whether additional information is attached to the surgical image, the determination being targeted for the target region.

(26)
The surgical information processing apparatus according to any one of (21) to (25),
wherein, in a case where the plurality of surgical images including a special light image and an observation light image are acquired, the determination unit
determines whether the additional information is attached by making a comparison using the observation light image.

(27)
The surgical information processing apparatus according to (26),
in which, in a case where the plurality of surgical images including the special light image being an infrared (IR) light image and the observation light image being a visible light image are acquired, the determination unit
determines whether the additional information is attached by making a comparison using the observation light image.

(28)
The surgical information processing apparatus according to any one of (21) to (27),
wherein the acquisition unit
acquires a first threshold being a threshold for a difference and a second threshold being a threshold for luminance, and
the determination unit
determines the additional information based on a comparison between a summed value of absolute differences of the plurality of surgical images and the first threshold and a comparison between a summed value of luminance values of the plurality of surgical images and the second threshold.

(29)
The surgical information processing apparatus according to (28),
in which the determination unit
discriminates a mask image and OSD information based on a comparison between a summed value of absolute differences of the plurality of surgical images and the first threshold and a comparison between a summed value of luminance values of the plurality of surgical images and the second threshold.

(30)
The surgical information processing apparatus according to (28) or (29),
in which the determination unit
determines the additional information by defining the summed value of absolute differences of the plurality of surgical images as a first axis and the summed value of luminance values of the plurality of surgical images as a second axis.

(31)
A surgical information processing method comprising:
acquiring a surgical image;
determining whether additional information is attached to the acquired surgical image; and
performing first image processing when it is determined that the additional information is not attached, and not performing the first image processing when determined that the additional information is attached.

(32)
A surgical information processing program comprising:
acquiring a surgical image;
determining whether additional information is attached to the acquired surgical image; and
performing first image processing when determined that the additional information is not attached, and not performing the first image processing when determined that the additional information is attached.

REFERENCE SIGNS LIST

1 SURGICAL INFORMATION PROCESSING SYSTEM
100, 100A SURGICAL INFORMATION PROCESSING APPARATUS
110 COMMUNICATION UNIT
120, 120A STORAGE UNIT
121 THRESHOLD INFORMATION STORAGE UNIT
122 PROCESSING CONDITION INFORMATION STORAGE UNIT
123 ADDITIONAL HISTORY INFORMATION STORAGE UNIT
130, 130A CONTROL UNIT
131 ACQUISITION UNIT
132 FIRST DETERMINATION UNIT
133, 133A SECOND DETERMINATION UNIT
134 PROCESSING UNIT
135 NOTIFICATION UNIT
136 TRANSMISSION UNIT

The invention claimed is:

1. A medical information processing apparatus comprising:
circuitry configured to
acquire a medical image;
determine whether additional information is attached to the medical image acquired;
on condition that the additional information is attached to the medical image, determine presence of a superimposition region between the medical image and the additional information;
perform first image processing when determined that the additional information is not attached;
perform first image processing on an entire portion of the medical image when determined that the additional information is attached and no superimposition region is present;
does not perform the first image processing on the entire portion of the medical image when determined that the additional information is attached and a superimposition region is present; and
perform second image processing to the medical image when determined that the additional information is attached and a superimposition region is present.

2. The medical information processing apparatus according to claim 1,
wherein the circuitry is configured to acquire the medical image from a medical observation device.

3. The medical information processing apparatus according to claim 1, wherein
not performing the first image processing includes the first image processing targeted for a region in the medical image other than the superimposition region.

4. The medical information processing apparatus according to claim 1, wherein the second image processing is of a type different from the type of the first image processing, the second image processing being targeted for a region of the additional information when determined that the additional information is attached.

5. The medical information processing apparatus according to claim 1,
wherein the circuitry is configured to
acquire metadata of the medical image, and
determine whether the additional information is attached to the medical image based on the metadata acquired.

6. The medical information processing apparatus according to claim 1,
wherein the circuitry configured to determine whether the additional information is attached to the medical image based on a result of image analysis on the medical image.

7. The medical information processing apparatus according to claim 1,
wherein the circuitry is configured to
acquire user setting information indicating settings made by a user, and
determine whether the additional information is attached to the medical image based on the user setting information acquired.

8. The medical information processing apparatus according to claim 1,
wherein the circuitry is configured to
acquire connected device information indicating a device connected to the medical information processing apparatus, and
determine whether the additional information is attached to the medical image based on the connected device information acquired.

9. The medical information processing apparatus according to claim 1,
wherein the circuitry is configured to determine a region of the additional information attached to the medical image.

10. The medical information processing apparatus according to claim 9,
wherein the circuitry is configured to determine a region of the additional information being character information attached to the medical image.

11. The medical information processing apparatus according to claim 1,
wherein the first image processing includes at least one of zoom, camera shake correction, rotation correction, or Picture in Picture (PinP).

12. The medical information processing apparatus according to claim 1,
wherein the circuitry is configured to
acquire a plurality of medical images including the medical image, and
determine whether additional information is attached to the medical image by comparing the plurality of medical images.

13. The medical information processing apparatus according to claim 12,
wherein the circuitry is configured to determine a portion in which a difference between pixel values of the plurality of medical images does not exceed a threshold as additional information.

14. The medical information processing apparatus according to claim 13,
wherein the circuitry is configured to make a determination by changing the threshold according to a device that has captured the medical image.

15. The medical information processing apparatus according to claim 12,
wherein the circuitry is configured to
acquire a target region that displays the additional information corresponding to a device that has captured the medical image, and
determine whether additional information is attached to the medical image, the determination being targeted for the target region.

16. The medical information processing apparatus according to claim 12, wherein, in a case where the plurality of medical images including a special light image and an observation light image are acquired, the circuitry is configured to determine whether the additional information is attached by making a comparison using the observation light image.

17. The medical information processing apparatus according to claim 12,
wherein the circuitry is configured to
acquire a first threshold being a threshold for a difference and a second threshold being a threshold for luminance, and
determine the additional information based on a comparison between a summed value of absolute differences of the plurality of medical images and the first threshold and a comparison between a summed value of luminance values of the plurality of medical images and the second threshold.

18. A medical information processing method comprising:
acquiring a medical image;
determining whether additional information is attached to the acquired medical image;
in response to determining that the additional information is attached to the medical image, determining presence of a superimposition region between the medical image and the additional information;
performing first image processing in response to determining that the additional information is not attached;
performing first image processing on an entire portion of the medical image in response to determining that the additional information is attached and no superimposition region is present;
not performing the first image processing on the entire portion of the medical image in response to determining that the additional information is attached and a superimposition region is present; and
performing second image processing to the medical image in response to determining that the additional information is attached and a superimposition region is present.

19. The medical information processing method according to claim 18, further comprising:
acquiring a plurality of medical images including the medical image; and
determining whether additional information is attached to the medical image by comparing the plurality of medical images by determining a portion in which a difference between pixel values of the plurality of medical images does not exceed a threshold as additional information.

20. A non-transitory computer-readable recording medium storing instructions for executing a method for processing medical information, the method comprising:
acquiring a medical image;
determining whether additional information is attached to the acquired medical image;
in response to determining that the additional information is attached to the medical image, determining presence of a superimposition region between the medical image and the additional information;
performing first image processing in response to determining that the additional information is not attached;
medical first image processing on an entirety of the medical image the medical image in response to determining that the additional information is attached and no superimposition region is present;
not performing the first image processing on the entirety of the medical image in response to determining that the additional information is attached and a superimposition region is present; and
perform second image processing to the medical image when determined that the additional information is attached and a superimposition region is present.

* * * * *